United States Patent
Xia et al.

(10) Patent No.: US 11,413,302 B2
(45) Date of Patent: Aug. 16, 2022

(54) USE OF CARRIMYCIN OR ACTIVE INGREDIENTS THEREOF AND USE THEREOF

(71) Applicant: SHENYANG FUYANG PHARMACEUTICAL TECHNOLOGY CO., LTD., Liaoning (CN)

(72) Inventors: Mingyu Xia, Liaoning (CN); Xiaofeng Zhao, Liaoning (CN); Xunlei Jiang, Liaoning (CN); Xundong Jiang, Liaoning (CN)

(73) Assignee: SHENYANG FUYANG PHARMACEUTICAL TECHNOLOGY CO., LTD., Liaoning (CN)

( * ) Notice: Subject to any disclaimer, the term of this patent is extended or adjusted under 35 U.S.C. 154(b) by 42 days.

(21) Appl. No.: 16/962,592

(22) PCT Filed: Jan. 18, 2019

(86) PCT No.: PCT/CN2019/072413
§ 371 (c)(1),
(2) Date: Jul. 16, 2020

(87) PCT Pub. No.: WO2019/141256
PCT Pub. Date: Jul. 25, 2019

(65) Prior Publication Data
US 2020/0338107 A1 Oct. 29, 2020

(30) Foreign Application Priority Data

Jan. 19, 2018 (CN) .......................... 201810052558.2
Jan. 19, 2018 (CN) .......................... 201810052732.3
Jan. 19, 2018 (CN) .......................... 201810053060.8

(51) Int. Cl.
*A61K 31/7048* (2006.01)
*A61P 25/28* (2006.01)
*A61K 45/06* (2006.01)

(52) U.S. Cl.
CPC .......... *A61K 31/7048* (2013.01); *A61P 25/28* (2018.01); *A61K 45/06* (2013.01)

(58) Field of Classification Search
CPC ....... C07H 17/08; A61K 31/7048; A61P 3/10; A61P 25/28
See application file for complete search history.

(56) References Cited

U.S. PATENT DOCUMENTS

| | | | |
|---|---|---|---|
| 2005/0197379 A1 | 9/2005 | Summers et al. | |
| 2013/0065848 A1* | 3/2013 | Jiang | C12N 9/1029 514/30 |
| 2013/0150316 A1 | 6/2013 | Jiang et al. | |
| 2013/0303600 A1 | 11/2013 | Ji et al. | |
| 2015/0344515 A1 | 12/2015 | Kellenberger et al. | |
| 2017/0231927 A1* | 8/2017 | Kagan | A61K 9/5078 424/452 |
| 2020/0030351 A1 | 1/2020 | Jiang et al. | |

FOREIGN PATENT DOCUMENTS

| | | |
|---|---|---|
| CN | 1554355 A | 12/2004 |
| CN | 1934117 A | 3/2007 |
| CN | 101568343 A | 10/2009 |
| CN | 101773510 A | 7/2010 |
| CN | 101785778 A | 7/2010 |
| CN | 101785779 A | 7/2010 |
| CN | 104837855 A | 8/2015 |
| EP | 2 578 596 A1 | 4/2013 |
| EP | 3 741 374 A1 | 11/2020 |
| JP | 2013-528166 A | 7/2013 |
| JP | 2013-528167 A | 7/2013 |
| RU | 2 593 498 C2 | 8/2016 |
| WO | 2011/110084 A1 | 9/2011 |
| WO | 2018-184587 A1 | 10/2018 |
| WO | 2019007368 A1 | 1/2019 |

OTHER PUBLICATIONS

Klimova, B. et al "Anti-aging drugs . . . " Curr. Med. Chem., vol. 25, No. 17, pp. 1946-1953. (Year: 2018).*
Kulkarni, A. et al "Benefits of metformin . . . " Cell Metab., vol. 32, pp. 15-30. (Year: 2020).*
Mack, H. et al "The nematode Caenorhabiditis elegans . . . " Drug Disc. Today, vol. 27, pp. 3-13. (Year: 2018).*
Bulterijs, S. et al "Phenotypic screening in *C. elegans* . . . " Pharmaceuticals, vol. 134, No. 13, pp. 1-35. (Year: 2020).*
Vaiserman, A. et al "Anti-aging pharmacology . . . " Ageing Res. Rev., vol. 31, pp. 9-35. (Year: 2016).*
Office Action dated Nov. 16, 2021, by the Japanese Patent Office in corresponding Japanese Patent Application No. 2020-539282. (5 pages).
International Search Report (PCT/ISA/210) dated Apr. 9, 2019, by the Chinese Patent Office as the International Searching Authority for International Application No. PCT/CN2019/072413.
Written Opinion (PCT/ISA/237) dated Apr. 9, 2019, by the Chinese Patent Office as the International Searching Authority for International Application No. PCT/CN2019/072413.

* cited by examiner

*Primary Examiner* — Leigh C Maier
(74) *Attorney, Agent, or Firm* — Buchanan Ingersoll & Rooney PC

(57) ABSTRACT

A medicament for preventing and/or treating a disease is disclosed, the disease is Alzheimer's disease, diabetes or senility; and the medicament includes a first active ingredient, and the first active ingredient includes one of carrimycin, isovalerylspiramycin I, isovalerylspiramycin II and isovalerylspiramycin III, or a combination of two or three of isovalerylspiramycin I, isovalerylspiramycin II and isovalerylspiramycin III.

16 Claims, 10 Drawing Sheets

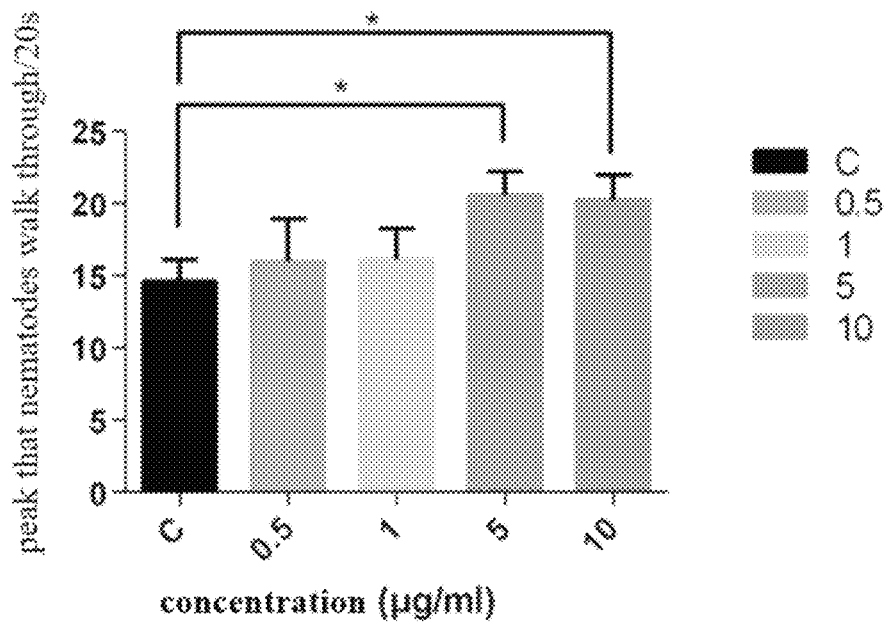
Fig. 11-a
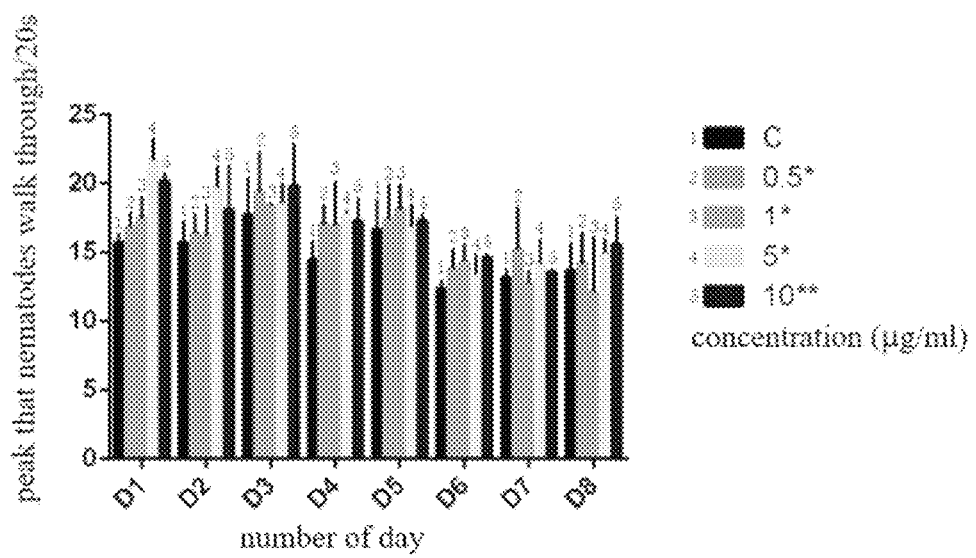
Fig. 11-b

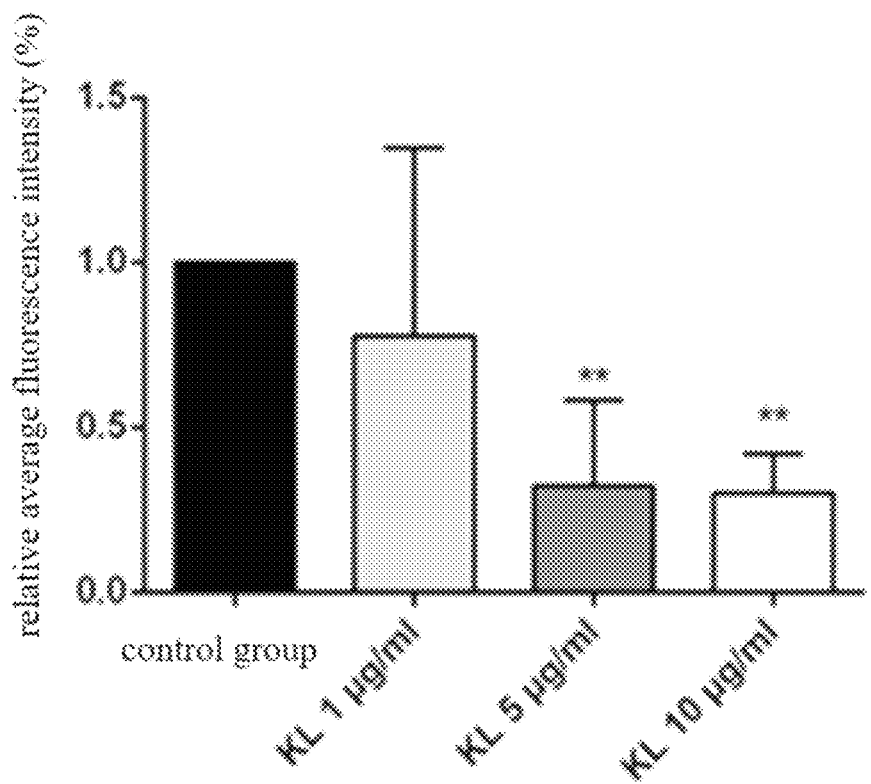
Fig. 14-a
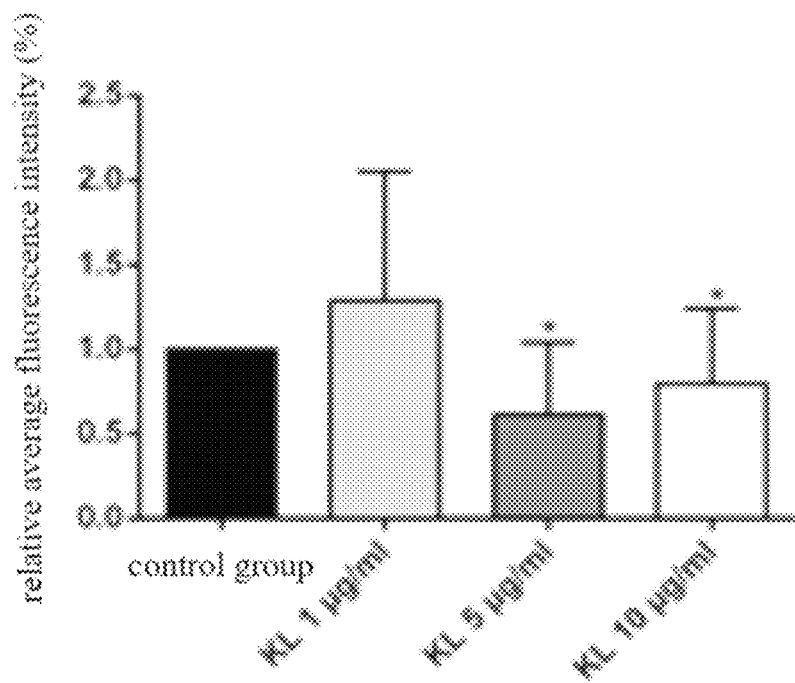
Fig. 14-b

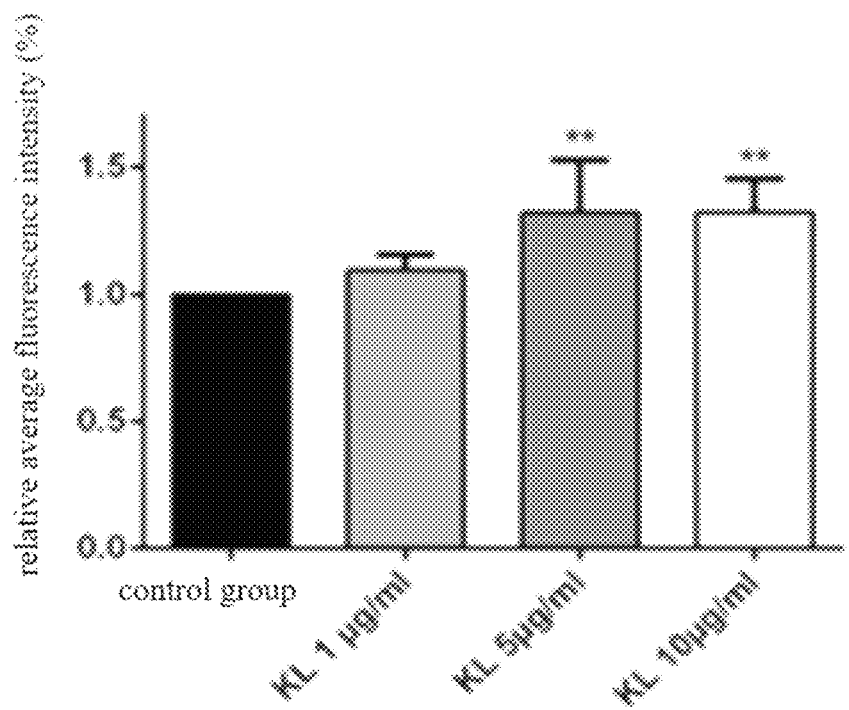
Fig. 15
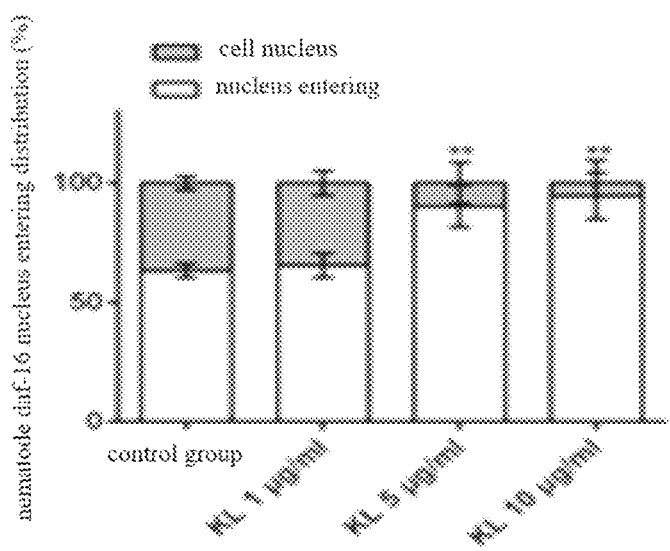
Fig. 16-a

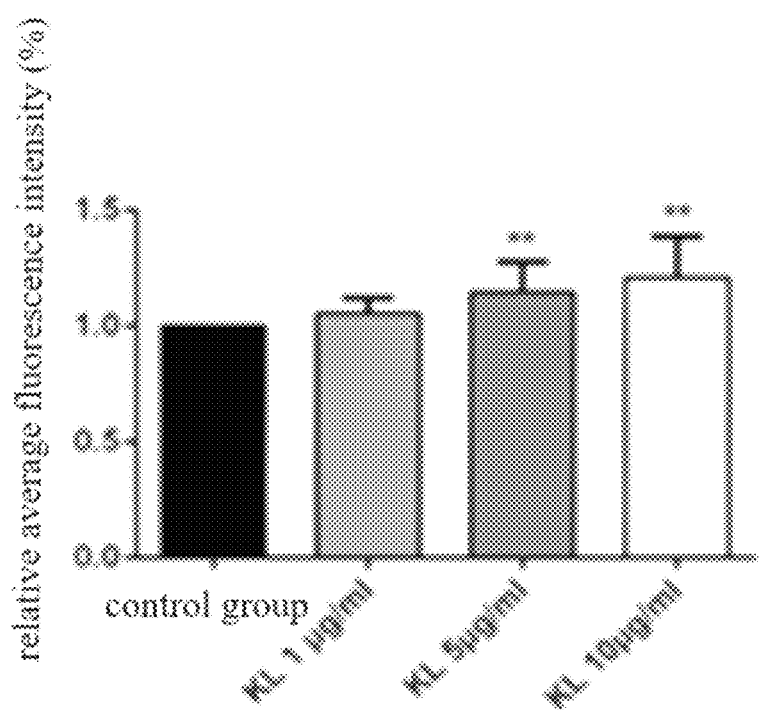
Fig. 16-b

USE OF CARRIMYCIN OR ACTIVE INGREDIENTS THEREOF AND USE THEREOF

TECHNICAL FIELD

The present disclosure relates to the field of drugs, and particularly relates to a use of carrimycin or active ingredients thereof.

BACKGROUND

Carrimycin is a novel antibiotic, which is formed by cloning the 4"-o-acyl-transferase group of carbomycin producing strain into spiramycin producing strain by using transgenic technique, directionally acylating the spiramycin 4"-OH, and adding an isovaleryl side chain at the 4" position and contains the 4" position isovalerylspiramycin as the major ingredient.

Carrimycin is composed of a variety of spiramycin derivatives, with the total content of the main active ingredients isovalerylspiramycin (I+II+III) not less than 60%, and it is a pharmaceutically acceptable drug composition. The core structure is a 16-membered lactonic ring, which is connected with a molecule of forosamine, a molecule of mycaminose and a molecule of mycarose. The major ingredients isovalerylspiramycin I, II and III differ from spiramycin in the structures in that the group connected to the 4" position of mycarose is an isovaleryl, rather than a hydroxyl. The drug has been applied for 1.1-type new drug jointly by Shenyang Tonglian Pharmaceutical and other entities.

The chemical structure of the major ingredients of carrimycin is as shown in Formula (1):

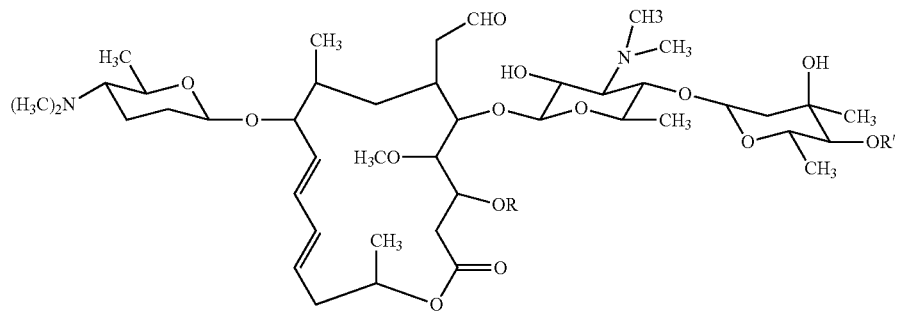

Formula (I)

wherein when R=H and R'=COCH$_2$CH(CH$_3$)$_2$, the formula represents isovalerylspiramycin I;

when R=COCH$_3$ and R'=COCH$_2$CH(CH$_3$)$_2$, the formula represents isovalerylspiramycin II; and when R=COCH$_2$CH$_3$ and R'=COCH$_2$CH(CH$_3$)$_2$, the formula represents isovalerylspiramycin III.

Carrimycin is a 16-membered-macrolide type antibiotic, has the active groups carboxyl, alkoxy, epoxy group, ketone group, formyl group and a pair of conjugated C=C, and has a molecular weight of approximately 884~982. Because of the similar chemical structures, carrimycin and macrolide-type antibiotics have many common properties: they are easily soluble in most organic solvents such as esters, acetone, chloroform and alcohols, are slightly soluble in petroleum ether, and insoluble in water; their molecular structures contain two dimethylamino groups and is weakly alkaline, and thus they are easily soluble in acidic aqueous solutions. They have a "negative solubility" property in which the solubility decreases with the increasing of the temperature. Because the major ingredient isovalerylspiramycin of carrimycin has a long carbon chain at the 4" position, it has a poor hydrophilicity, and its solubility in water is lower than those of spiramycin and 4"-acetyl spiramycin.

Carrimycin is a white amorphous powder, with a slight hygroscopicity, a specific rotation of approximately-80.8°, and an ultraviolet maximum absorption wavelength of 231~232 nm. It has a weak fluorescence chromophoric group itself, and presents a violet reaction when contacting concentrated sulphuric acid or hydrochloric acid, to generate an intensive violet fluorescence, with a maximum value of light absorption at 231~232 nm.

The drug has a good lipophilicity, a strong capacity of tissue penetration, a quick oral absorption, a long in-vivo maintaining duration, and a persistent post-antibiotic effect. According to the relation between the efficacy and the chemical conformation, after the acylation of the 4" position of the macrolide-type antibiotics, the lipophilicities and in-vivo activities of them are improved, the in-vivo antibacterial activities and the clinical treatment effects are significantly improved, and the in-vivo stabilities of the antibiotics are increased with the prolonging of the carbon chain of the 4" position hydroxyl ester, i.e., isovalerylspiramycin>butyryl spiramycin>propionyl spiramycin>acetyl spiramycin.

The preliminary in vitro and vivo pharmacodynamic experiments show that the drug does not only have a good antibacterial activity on a majority of G$^+$ bacteria, but also has a certain effect on some G$^-$ bacteria; various technical indexes of the drug are obviously superior to those of azithromycin, erythromycin, acetyl spiramycin and medemycin; especially, it has the strong antibacterial activity on mycoplasma pneumoniae; it also has a certain antibacterial activity on erythromycin drug-resistance bacteria, *Neisseria gonorrhoeae, Streptococcus pneumoniae, Staphylococcus aureus, Pseudomonas aeruginosa, Bacillus influenzae, Haemophilus influenzae, Bacteroides fragilis, Legionella pneumophilia, Bacteroides thetaiotaomicron* and *Clostridium perfringens;* and it has merely little cross resistance on *Staphylococcus aureus,* which is clinically resistant to erythromycin. Carrimycin will be mainly used to treat infectious diseases caused by gram-positive bacteria, especially upper respiratory tract infection, and may be used to treat urinary system infection and so on.

The applicant has found out in a recent study that carrimycin or its active ingredients isovalerylspiramycin I, isovalerylspiramycin II and isovalerylspiramycin III or combinations thereof have a good effect in resisting senility, resisting diabetes or resisting Alzheimer's disease, which provides the theoretical basis for the clinical promotion of the drug Carrimycin or its drug active ingredients, and has important economic benefits and social benefits.

In view of that, the present disclosure has been proposed.

SUMMARY

An object of the present disclosure is to provide a drug for preventing and/or treating a disease.

In order to achieve the above object, the present disclosure adopts the following technical solutions:

A medicament for preventing and/or treating a disease is provided, the disease is Alzheimer's disease, diabetes or senility; and the medicament comprises a first active ingredient, and the first active ingredient comprises one of carrimycin, isovalerylspiramycin I, isovalerylspiramycin II and isovalerylspiramycin III, or a combination of two or three of isovalerylspiramycin I, isovalerylspiramycin II and isovalerylspiramycin III.

Further, the medicament further comprises a second active ingredient;

preferably, when the disease is Alzheimer's disease, the second active ingredient is at least one of anti-Alzheimer-disease drugs;

when the disease is diabetes, the second active ingredient is at least one of antidiabetic drugs; and when the disease is senility, the second active ingredient is at least one of drugs for delaying senility or prolonging life span.

Further, the medicament and a pharmaceutically acceptable carrier are made into a clinically acceptable preparation, preferably a tablet, a capsule, a pill, an injection, a sustained-release preparation or a particulate administration system.

Further, a dosage of the drug is in a range from 10 to 1500 mg/kg, preferably from 50 to 1000 mg/kg, more preferably from 100 to 500 mg/kg.

The present disclosure further provides a combined product for preventing and/or treating a disease, the disease is Alzheimer's disease, diabetes or senility; and the combined product comprises a first medicament, and an active ingredient of the first medicament comprises one of carrimycin, isovalerylspiramycin I, isovalerylspiramycin II and isovalerylspiramycin III, or a combination of two or three of isovalerylspiramycin I, isovalerylspiramycin II and isovalerylspiramycin III.

Further, the combined product further comprises a second medicament;

preferably, when the disease is Alzheimer's disease, the second medicament is at least one of drugs for preventing and/or treating Alzheimer's disease;

when the disease is diabetes, the second medicament is at least one of drugs for preventing and/or treating diabetes; and when the disease is senility, the second medicament is at least one of drugs for delaying senility or prolonging life span.

Further, an amount ratio of the first medicament to the second medicament is 1~99:99~1, preferably 5~95:95~5, more preferably 10~90:90~10, most preferably 20~80: 80~20.

Further, the drugs for preventing and/or treating Alzheimer's disease include a drug acting on a cholinergic system, a drug acting on an N-methyl-D-aspartate receptor, an antioxidant drug, an anti-inflammatory drug, a drug inhibiting formation of Aβ protein, estrogen, nerve growth factor, Nimodipine and an antiapoptotic agent; and the drugs for preventing and/or treating diabetes include at least one of a biguanide hypoglycemic drug, a sulfonylurea hypoglycemic drug, an α-glycosidase inhibitor, an insulin sensitizer, a non-sulfonylurea insulin secretagogues agent and insulin.

The present disclosure further provides a use of the medicament or the combined product in manufacturing medicament for preventing and/or treating Alzheimer's disease, promoting intelligence, preventing and/or treating diabetes, delaying senility or prolonging life span.

Particularly, the use in manufacturing medicament for preventing and/or treating Alzheimer's disease and promoting intelligence includes a use in manufacturing medicament for reducing hydrolysis of acetylcholine, a use in manufacturing medicament for ameliorating cognitive disorder and dyskinesia, a use in manufacturing medicament for protecting intracerebral nerve cell, and a use in manufacturing medicament for not reducing body weight, improving immunity or improving leukocyte.

The use in manufacturing medicament for preventing and/or treating diabetes includes a use in manufacturing medicament for preventing and/or treating diabetes type I or diabetes type II or specific types of diabetes, preferably a use in manufacturing medicament for facilitating insulin secretion or reducing blood sugar or protecting islet β cell or a use in manufacturing medicament for preventing and/or treating diabetes and maintaining body weight.

The use in manufacturing medicament for delaying senility or prolonging life span includes a use in manufacturing medicament for delaying senility and/or prolonging life span by changing an activity of a transcription factor DAF-16; a use in manufacturing medicament for delaying senility and/or prolonging life span by improving an expression level of SIR2.1 as a homologous protein of SIR2 and influencing an activity of the DAF-16 by the SIR2.1; or a use in manufacturing medicament for delaying senility and/or prolonging life span by activating AMPK to directly increase an activity of FOXO/DAF-16.

The present disclosure is described in detail below:

A first object of the present disclosure is to provide a drug for preventing and/or treating Alzheimer's disease.

In order to achieve the above object, the present disclosure employs the following technical solutions:

The present disclosure provides a drug for preventing and/or treating Alzheimer's disease, and an effective ingredient of the drug comprises one of carrimycin, isovalerylspiramycin III, isovalerylspiramycin II and isovalerylspiramycin I, or the combination of two or three of isovalerylspiramycin I, isovalerylspiramycin II and isovalerylspiramycin III.

Carrimycin is the mixture of various active ingredients, and, besides the three active ingredients isovalerylspiramycin I, isovalerylspiramycin II and isovalerylspiramycin III, contains impurity.

Further, the drug comprises a pharmaceutically acceptable carrier.

Further, the drug is formulated into a clinically acceptable tablet, capsule, pill, injection, sustained-release preparation or particulate administration system.

Further, the dosage of the drug is in a range from 10 to 1500 mg/kg.

Further, the dosage of the drug is in a range from 50 to 1000 mg/kg.

Further, the dosage of the drug is in a range from 100 to 500 mg/kg.

The present disclosure further provides a combined product for preventing and/or treating Alzheimer's disease. The combined product comprises a first medicament, and an active ingredient of the first medicament comprises one of carrimycin, isovalerylspiramycin III, isovalerylspiramycin II and isovalerylspiramycin I, or the combination of two or three of isovalerylspiramycin I, isovalerylspiramycin II and isovalerylspiramycin III.

Further, the combined product further comprises a second medicament.

Further, the second medicament comprises at least one of drugs for preventing and/or treating Alzheimer's disease.

Further, the drugs for preventing and/or treating Alzheimer's disease include a drug acting on a cholinergic system, a drug acting on an N-methyl-D-aspartate receptor, an antioxidant drug, an anti-inflammatory drug, a drug inhibiting formation of Aβ protein, estrogen, nerve growth factor, Nimodipine and an antiapoptotic agent.

The present disclosure further provides the use of any one of the above drug or combined product in preventing and/or treating Alzheimer's disease and promoting intelligence.

Alzheimer's disease (AD) is a neurodegenerative disease with progressive dementia as the major clinical manifestation. The hypothesis of cholinergic injury is a theory of Alzheimer's disease (AD) that has been generally acknowledged early, and cholinergic injury is considered as an important etiology of AD. The cholinergic system is considered as an important target spot of drugs for AD. Experimentation indicates that the drug in the present disclosure, by reducing the hydrolysis of acetylcholine, increases the contents of acetylcholine in cerebral hippocampus and cerebral cortex, thereby improving the cognitive function, and realizing the preventing and/or treating of Alzheimer's disease.

The present disclosure further provides the use of any one of the above drug or combined product in reducing hydrolysis of acetylcholine.

The present disclosure further provides the use of any one of the above drug or combined product in ameliorating cognitive disorder and dyskinesia.

The present disclosure further provides the use of any one of the above drug or combined product in protecting intracerebral nerve cell.

The present disclosure further provides the use of any one of the above drug or combined product in not reducing body weight, improving immunity and improving leukocyte.

A second object of the present disclosure is to provide a drug for preventing and/or treating diabetes.

In order to achieve the second object of the present disclosure, the present disclosure employs the following technical solutions:

A drug for preventing and/or treating diabetes is provided, the effective ingredient of the drug comprises one of carrimycin, isovalerylspiramycin I, isovalerylspiramycin II and isovalerylspiramycin III, or the combination of two or three of isovalerylspiramycin I, isovalerylspiramycin II and isovalerylspiramycin III.

The drug according to the present disclosure comprises a pharmaceutically acceptable carrier.

The drug according to the present disclosure may be formulated by using a pharmaceutically acceptable carrier into a tablet, a capsule, a pill, an injection, a sustained-release preparation or a particulate administration system.

The dosage of the effective ingredient of the drug according to the present disclosure is in a range from 10 to 1500 mg/kg, preferably in a range from 50 to 1000 mg/kg, more preferably in a range from 100 to 500 mg/kg.

The diabetes is diabetes type I or diabetes type II or specific types of diabetes. Diabetes has many pathogenesis, and the drug for preventing and/or treating diabetes according to the present disclosure mainly aims at the diabetes caused by the following factors: imbalance of Th1 and Th2 cells and their expression factors, loss of β cell caused by invasion into the organism by viruses, overexpression of UCP2 gene or mutation of autosome.

The present disclosure further provides a combined product for preventing and/or treating diabetes, the combined product comprises a first medicament, and the effective ingredient of the first medicament comprises one of Carrimycin, isovalerylspiramycin I, isovalerylspiramycin II and isovalerylspiramycin III, or the combination of two or three of isovalerylspiramycin I, isovalerylspiramycin II and isovalerylspiramycin III.

The combined product according to the present disclosure further comprises a second medicament, the second medicament comprises at least one of drugs that are capable of treating diabetes.

Preferably, the second medicament comprises at least one of a biguanide hypoglycemic drug, a sulfonylurea hypoglycemic drug, an α-glycosidase inhibitor, an insulin sensitizer, a non-sulfonylurea insulin secretagogues agent and insulin.

Preferably, the amount ratio of the first medicament to the second medicament is 1~99:99~1, preferably 5~95:95~5, more preferably 10~90:90~10, most preferably 20~80:80~20.

The present disclosure further provides the use of at least one of carrimycin, isovalerylspiramycin I, isovalerylspiramycin II and isovalerylspiramycin III in manufacturing medicament for preventing and/or treating diabetes; and the diabetes is diabetes type I or diabetes type II or specific types of diabetes.

The present disclosure further provides the use of at least one of carrimycin, isovalerylspiramycin I, isovalerylspiramycin II and isovalerylspiramycin III in manufacturing medicament for facilitating insulin secretion or reducing blood sugar or protecting islet β cell.

The present disclosure further provides the use of at least one of carrimycin, isovalerylspiramycin I, isovalerylspiramycin II and isovalerylspiramycin III in manufacturing medicament for preventing and/or treating diabetes and maintaining body weight.

A third object of the present disclosure is to provide a drug for delaying senility and/or prolonging life span.

In order to achieve the third object of the present disclosure, the present disclosure employs the following technical solutions:

A composition for delaying senility and/or prolonging life span is provided, the composition comprises a first active ingredient, and the first active ingredient is one of carrimycin, isovalerylspiramycin I, isovalerylspiramycin II and isovalerylspiramycin III, or the combination of two or three of isovalerylspiramycin I, isovalerylspiramycin II and isovalerylspiramycin III.

Further, the composition further comprises a second active ingredient.

Further, the second active ingredient comprises at least one of drugs for delaying senility or prolonging life span.

In the present disclosure, at least one of the first active ingredients and at least one of the second active ingredients may be formulated into a compound preparation.

Further, in the formulating of the compound preparation, the amount ratio of the first active ingredient to the second active ingredient is 1~99:99~1, preferably 5~95:95~5, more preferably 10~90:90~10, most preferably 20~80:80~20.

Further, the composition is formulated by using an acceptable excipient into a drug, a health-care product or a food additive.

Further, the drug is a pharmaceutically acceptable formulation.

Further, the pharmaceutically acceptable formulation is a tablet, a capsule, a pill, an injection, a sustained-release preparation or a particulate administration preparation.

The present disclosure further provides a combined product for delaying senility and/or prolonging life span, the combined product comprises a first medicament, and the active ingredient of the first medicament comprises one of carrimycin, isovalerylspiramycin I, isovalerylspiramycin II and isovalerylspiramycin III, or the combination of two or three of isovalerylspiramycin I, isovalerylspiramycin II and isovalerylspiramycin III.

In the present disclosure, carrimycin is the mixture of various active ingredients, and, besides the three active ingredients isovalerylspiramycin I, isovalerylspiramycin II and isovalerylspiramycin III, contains impurity.

Further, the combined product further comprises a second medicament.

Further, the second medicament comprises at least one of drugs for delaying senility or prolonging life span.

In the present disclosure, the first medicament and the second medicament may be administered in combination. In the combined administration, the first medicament and the second medicament do not have a prescribed administration order, wherein the first medicament may be administered firstly, the second medicament may be administered firstly, and the two medicaments may be administered simultaneously.

In the combined administration, the amount ratio of the first medicament to the second medicament is 1~99:99~1, preferably 5~95:95~5, more preferably 10~90:90~10, most preferably 20~80:80~20.

Further, the first medicament is a pharmaceutically acceptable formulation.

Further, the pharmaceutically acceptable formulation is a tablet, a capsule, a pill, an injection, a sustained-release preparation or a particulate administration preparation.

The present disclosure further provides the use of the composition or the combined product in preparation of a product for delaying senility and/or prolonging life span.

Particularly, the present disclosure relates to the use of the composition or the combined product in manufacturing medicament for delaying senility and/or prolonging life span by changing the activity of a transcription factor DAF-16; the use in manufacturing medicament for delaying senility and/or prolonging life span by improving the expression level of SIR2.1 as a homologous protein of SIR2 and influencing the activity of the DAF-16 by the SIR2.1; or the use in manufacturing medicament for delaying senility and/or prolonging life span by activating AMPK to directly increase the activity of FOXO/DAF-16, of the combined product.

Further, the product is a drug, a health-care product or a food additive.

The study selects wild-type *Caenorhabditis elegans*, which is divided into the administration group and the blank control group; firstly administers with different concentrations and measures the growth curves of the nematodes, investigates the influence by carrimycin on the physiological indexes related to the life span, such as the variations of the egg laying amount and the action and movement capacity of the nematodes; and further measures, after the administration of carrimycin, the survival rates of the nematodes after high-temperature stress at 37° C. and ultraviolet irradiation and stimulation.

The usage of the nematode to the model of senility resistance has the following advantages:

Because 60%-80% of the genes of the nematode highly conserve with the relative genes of human being, and the nematode has twelve of the signal transduction pathways that have been found out so far. The present disclosure utilizes *Caenorhabditis elegans* as the model organism for screening the senility resisting drug. The suitable mutant may be selected by using the rich genetic resource of the nematode according to the research purpose, to study the mechanisms of senility and senility resistance. In fact, all of the several main theories of the mechanism of senility are proved in nematodes. Therefore, drugs that have the effect of resisting senility for nematodes are usually considered to have the same efficacy for human being.

The usage of *Caenorhabditis elegans* for life analysis has had a history of 30 years so far. Because of its unique advantages, it has become the firstly chosen model for studies on senility. The nematode has a short generation cycle, which is generally approximately 3 days, and a short life, which is generally approximately 3 weeks. That enables the repeatability and stability of the experiments. In order to guarantee the reliability of the experimental approaches and the accuracy of the experimental results and guarantee that the drug screening can obtain more accurate and credible information, it is necessary to repeat the experiments. Because *Caenorhabditis elegans* has the above unique advantages, it has become the firstly chosen model for studies on senility. Therefore, the nematode can be used to assess the effect of resisting senility of the composition, and in turn determine that the composition can be used to formulate senility resisting drugs.

The results of the study indicate that Carrimycin has the effect of resisting senility to *Caenorhabditis elegans*.

In the present disclosure, the drug may be formulated by using conventional methods in the art into various pharmaceutically acceptable formulations, such as a tablet and a capsule.

In the present disclosure, the dosage of the drug is in a range from 10 to 1500 mg/kg, preferably in a range from 50 to 1000 mg/kg, more preferably in a range from 100 to 500 mg/kg.

The present applicant has proved by experimentation that carrimycin or its drug active ingredients isovalerylspiramycin I, isovalerylspiramycin II and isovalerylspiramycin III or combinations thereof have a good effect in resisting Alzheimer's disease, resisting diabetes or resisting senility, which provides the theoretical basis for the clinical promotion of the drug carrimycin or its drug active ingredients, and has important economic benefits and social benefits.

BRIEF DESCRIPTION OF THE DRAWINGS

FIG. 11-a is the assay of the movement indicator after the administration of 5 μg/ml of carrimycin;

FIG. 11-b is the assay of the movement indicator after the administration of 10 μg/ml of carrimycin;

FIG. 14-a is the assay of the fluorescence intensity on the 10th day after the administration of carrimycin;

FIG. 14-b is the assay of the fluorescence intensity on the 15th day after the administration of carrimycin;

FIG. 15 is the assay of the fluorescence intensity after the administration of carrimycin;

FIG. 16-a is the assay of the state of nucleus entering of TJ356 nematode DAF-16 on the 6th day after the administration of carrimycin; and FIG. 16-b is the assay of the fluorescence intensity of the TJ356 nematodes on the 6th day after the administration of carrimycin;

Figure 1:
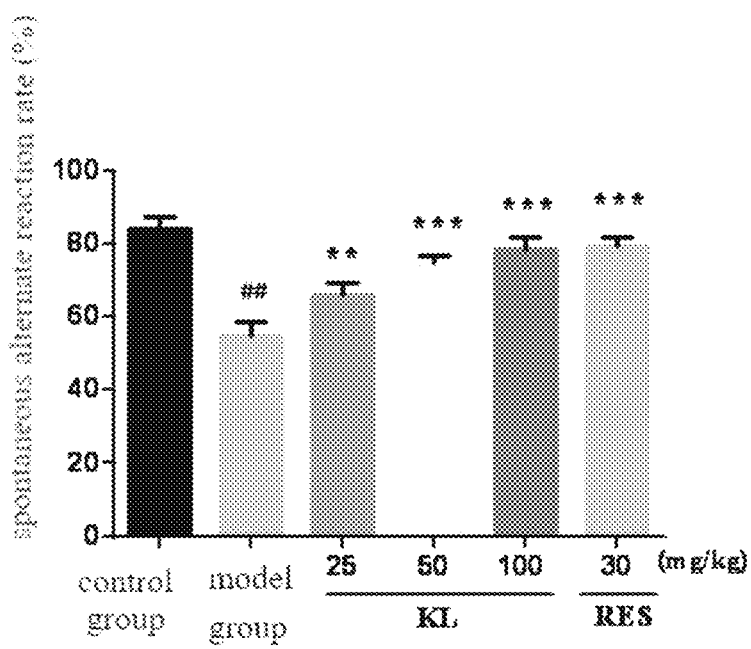
FIG. 1 is the Y-maze spontaneous alternate reaction rates of the groups of rats in the rat Y-maze experiment according to the present disclosure.

wherein in the drawings, KL represents carrimycin, and RES represents resveratrol.

DETAILED DESCRIPTION

In order to make the objects, the technical solutions and the advantages of the examples of the present disclosure clearer, the technical solutions of the examples will be described clearly and completely below by referring to the examples of the present disclosure. The following examples are intended to explain the present disclosure, but are not intended to limit the scope of the present disclosure.

It should be noted that the drug Carrimycin described in the following examples may also refer to the composition of one or more of isovalerylspiramycin I, isovalerylspiramycin II and isovalerylspiramycin III.

EXAMPLE 1

Tablet of Carrimycin

Specification: 200 mg/350 mg
Prescription of the tablet core:

| | |
|---|---|
| Carrimycin | 200 g |
| microcrystalline cellulose | 110 g |
| sodium starch glycolate | 22 g |
| povidone K30 (5%) | 15 g |
| magnesium stearate | 3 g | formulated into 1000 tablets
Prescription of the coating solution:

| | |
|---|---|
| Opadry II | 21 g |
| Distilled water | proper amount formulated into 105 ml |

The preparation process:

Preparation of the tablet core: the main drug and the excipients respectively passed through a 100-meshes sieve, and a prescription dosage of carrimycin, a prescription dosage of microcrystalline cellulose and a ½ prescription dosage of sodium starch glycolate were uniformly mixed, then an aqueous solution of 5% povidone $K_{30}$ was added to prepare a soft material. A 18-mesh sieve was used for granulating, and the wet granules were dried under a ventilated condition at 60° C. for 2 h. After the wet granules were dried, a 18-mesh screen was used for dispersing the granules, then a ½ prescription dosage of sodium starch glycolate and a prescription dosage of magnesium stearate were added. And after the materials were uniformly mixed, and the mixture was tabletted by using a shallow concave die of the diameter of 11 mm, to obtain a drug containing tablet core with the tablet weight of 350 mg and the hardness of 6.5 kg.

Preparation of the coating solution: the required amount of Opadry II (white color) was weighed, the required amount of water was added into the preparation container in batches, the stirring speed was reduced to make the spiral disappear, and the stirring was continued to be performed for 30 min to obtain the coating solution.

Preparation of the film coated tablet: the tablet core was placed into a coating pan, the coating conditions were determined, and coating was carried out with the main rotation speed of 20 r/min, the air intake temperature of 40° C., the air outtake temperature of 30° C., the atomization pressure of 0.02 Mpa and the guniting flow rate of 1 ml/min. And after a constant state was achieved, the coating was continuously to be sprayed for 1.5 h to obtain a tablet with a smooth surface and a uniform tincture. The tablet were qualified if it were in compliance with the inspecting standards of thin-film coating. The coating adds the weight by approximately 5%.

EXAMPLE 2 tablet of Carrimycin (Calculated for 10000 Tablets)

Prescription:

| | |
|---|---|
| raw powder of Carrimycin | 1000 g |
| low-substituted hydroxypropyl cellulose (5%) | 92.5 g |
| sodium starch glycolate (3%) | 55.5 g |
| magnesium stearate (1%) | 18.5 g |
| starch | the total weight subtracts the weights of |

-continued

| | the other raw materials and excipients |
|---|---|
| total weight | 1850 g |

The preparation process: a proper amount of starch was weighed, diluted to the concentration of 15%, and heated to a paste to obtain an adhesive; the main material carrimycin and the excipients starch, low-substituted hydroxypropyl cellulose, sodium starch glycolate and magnesium stearate passed through a 100-meshes sieve, respectively; and prescription dosages of the main material and the excipients were weighed. After the drug A (carrimycin), starch and low-substituted hydroxypropyl cellulose were fully and uniformly mixed, the starch paste with the starch concentration of 15% was used to prepare the mixture into a soft material which was granulated by a 14-mesh sieve, and granules were dried at 50-60° C. to control the moisture content at 3-5%. A 14-mesh sieve was used for dispersing the granules, and then sodium carboxymethyl starch and magnesium stearate were added to be mixed, and the granule content was measured. The weight of the tablet was calculated according to the granule content, and the mixture was tabletted (with a Φ9 mm shallow concave punch), then the difference in the weight of the tablets was detected. After passing the test, the tablets were packaged.

EXAMPLE 3

Capsule of Carrimycin (Calculated for 10000 Granules)

Prescription:

| raw powder of Carrimycin | 1000 g |
|---|---|
| starch | 1080 subtracts the weight of the raw powder of the drug A |
| medicinal No. 3 capsule | 1000 granules |
| liquid paraffin | 50 ml |

Preparation process: the main material carrimycin and the adjuvant medicinal starch were separately weighed according to the process formula amount, and then fully mixed in a mixer for 1.5-2 hours. The data obtained by sampling and content testing should be basically consistent with the theoretical data (the weight of each capsule was about 0.105 g), and the qualified No. 3 medicinal capsule and the mixed raw materials to be loaded were filled in a filling device according to the operation requirements of an automatic capsule machine, and the filled capsules were subjected to a difference test (±10% or less, <0.3 g) to see if the dissolution rate meets the requirements or not. The capsules that meet the requirements after being tested were put into a polishing machine to be polished for 15-20 minutes with the liquid paraffin added, and then were taken out to be tested by finished product packaging boxes.

EXAMPLE 4

Dried Syrup of Carrimycin (calculated for 10000 Bags)

Prescription:

| raw powder of Carrimycin | 1250 g |
|---|---|
| citric acid (0.5%) | 15 g |
| sucrose | the total weight subtracts the weights of the other raw materials and excipients |
| total weight, approximately | 5000 g |
| pigment (Curcumin) | approximately 1 g |

Preparation process: the carrimycin raw powder, citric acid and sucrose were respectively grinded into granules by a high-speed jet mill, and 85% of the granules pass through a 300-mesh sieve, 15% of the granules pass through a 180-mesh sieve. Then the fine powder after grinding was weighed according to the prescription amount and fully mixed for 1-1.5 hours, the content was measured, the loading capacity was calculated (the theoretical loading capacity was 500 mg per bag). Then the mixture was put into a bagging machine, aluminum foil paper was installed, and filling was carried out according to the operation requirements of a filling machine. The difference was allowed to be within ±5%, and after the filling, the outer packaging was carried out after passing the inspection.

EXAMPLE 5

Granule Preparation of Carrimycin (Calculated for 10000 Bags)

Prescription:

| Raw powder of Carrimycin | 1250 g |
|---|---|
| sugar powder | 20000 g |
| dextrin | 9000 g |
| 5% PVP-K$_{30}$ | proper amount |

Preparation process: the carrimycin raw powder, the powdered sugar and the dextrin pass through a 120-mesh sieve, and the carrimycin, powdered sugar and dextrin were weighed according to the prescription amount and uniformly mixed. And the above uniformly mixed materials were made into a soft material with a 5% PVP-K30 mucilage, and then the soft material was granulated with a swinging granulation machine, dried at 70° C. and subjected to granule dispersion, and the resulting granules were subpackaged after being qualified for inspection.

EXAMPLE 6

Freeze-Dried Powder Injection of Carrimycin 500 mg of carrimycin raw powder was uniformly mixed with an equimolar amount of propylene glycol, and the mixture was dissolved in 5 ml of water to obtain a faint yellow clear solution having a pH between 4.6 and 5.6. Further, 40 mg of mannitol was added as a lyophilized proppant into the faint yellow clear solution, and after being frozen rapidly at a low temperature for 9 hours, the material was freeze-dried to obtain a faint yellow loose mass, which was dissolved in 10 ml of sterile water before being used.

TEST EXAMPLE 1

Determining, by Using Cell Experimentation, whether Carrimycin has the Function of Protecting Islet Cell The object of the test is to assess the function of the tested sample Carrimycin of in-vitro protection of islet β cell.

Cell Strain:

Rat insulinoma cell, or INS cell, commercially available from the Cell Resource Center of the Basic Medicine Research Institute of Chinese Academy of Medical Sciences.

Reagents:

RPMI1640 nutrient solution and fetal bovine serum are commercially available from the Gibco company in the United States, and trypsin, glutamine, penicillin, streptomycin, dimethyl sulfoxide (DMSO), methyl thiazolyl tetrazolium (MTT), alloxan (Alloxan monohydrate, purity≥98.0%) are commercially available from the Sigma company in the United States.

Instruments:

Carbon-dioxide incubator (Sanyo, Japan), enzyme linked immunosorbent assayer (Tecan, Austria), 96-well culture plate (Corning, USA), and inverted microscope (Motic, China).

The operation steps were as follows:

Adherent cell:

the INS-1 cell was the adherent cell, the INS-1 cell in the logarithmic growth phase was used, digested by using trypsin, beated by using a complete medium, and prepared into a single-cell suspension. The cell concentration was adjusted to be $1*10^5$/ml, and the cell was inoculated into the 96-well culture plate with 100 µl per well, cultured in the incubator at 5% $CO_2$ and 37° C. for 24 h. The cells were grouped according to the demands of the experiment, the cell of the administration groups were administered with 24 mmol/L of alloxan damage, simultaneously were administered with the drug to be tested Carrimycin with different concentrations (0.2, 0.4 and 0.8 mM), 4 complex wells for each of the concentrations were provided, and all groups were continued to be cultured at 37° C. for 24 h. Additionally a normal control group (no medication administered), a model group (merely administered with alloxan damage) and a positive control group (based on the alloxan treatment, 0.5 mmol/L of metformin was added) were provided. Then the supernatant of all groups were removed, and were washed carefully by using PBS for 3 times, each of the wells was added 100 µL newly formulated culture medium containing 0.5 mg/ml of MTT, the were continued to be cultured at 37° C. for 4 h. Then the supernatant of all groups were removed carefully, 150 mL of DMSO was added into each of the wells, and all groups were mixed uniformly by using a micro oscillator for 10 min. And the optical density of all groups were measured by using a microplate reader at 492 nm.

Assessment of the result:

The survival rate of the INS-1 cell treated by the drug is calculated by using the following formula:

Survival rate of INS cell (%)=$A_{492}$ (administration group)/$A_{492}$ (normal control group)×100%

Result: the result of the assessment of the protection by the drug to be tested on islet cell was as shown in the following Table 1:

TABLE 1

| protection by Carrimycin on INS-1 ($\bar{x} \pm s$) | | |
|---|---|---|
| Group | Dosage | Survival rate (%) |
| Normal control group | — | 100.00 |
| Model control group | — | 75.48 ± 4.23[*] |
| Positive control group | 0.5 mM | 92.91 ± 6.69[##] |
| Administration group | 0.2 mM | 89.87 ± 4.60[##] |
| | 0.4 mM | 93.28 ± 3.91[###] |
| | 0.8 mM | 97.73 ± 5.294[###] |

[*]$p < 0.05$ as compared with the normal control group, [##]$p < 0.01$ as compared with the model control group, [###]$p < 0.001$ as compared with the model control group, the sample exhibits a good effect of protection on INS-1 cell.

TEST EXAMPLE 2

The object of the test is to assess the effect of the sample to be test Carrimycin on the blood sugar of a diabetes mouse.

Reagents:

Alloxan (Alloxan monohydrate, purity≥98.0%) and metformin (purity 97%) are commercially available from the Sigma-Aldrich company.

The insulin measuring kit is commercially available from Shanghai Rongsheng Biotech Co., Ltd. (lot number: E0210006).

Instruments:

One-touch model blood-sugar detector and blood-sugar test paper (Johnson & Johnson, the United States), and electronic analytical balance.

Animal:

SPF-grape Kunming mice, with body weights of 18~20 g

Process:

The study on the effect of Carrimycin on reducing blood sugar comprises Kunming mice was selected, single intraperitoneal injection with 160 mg/kg of alloxan was subjected to Kunming mice to form model mice. The mice whose values of blood sugar are stable at the modeling level (10~25mmol/L) were selected, divided randomly into a model control group, a positive control group (200 mg/kg of metformin) and an administration group (with Carrimycin as the drug, 25, 50 and 100 mg/kg). Simultaneously a normal control group was provided, and was given gastric normal saline.

After the model was made and gavage was given for 30 and 45 days, the mice were fasted for 16 hours, and the mice were weighed. After weighing, blood was collected at the tail tip, and the fasting blood sugar was measured by using a blood-sugar meter. After the value of fasting blood sugar was measured, the rats were administered by intragastric administration once. After 2 h, mice in each group were given a glucose solution by gavage at 2 g/kg, and blood was collected at the tip of the tail. The blood sugar values at 0, 0.5 and 2 h were measured after the administration of glucose (Bg0, Bg0.5 and Bg2), and the area (AUC) (reaction sugar tolerance) under the blood sugar curve was calculated by using the following formula:

AUC=0.25*(Bg0+4*Bg0.5+3*Bg2); and

After the model was made and gavage was given for 45 days, the mice were fasted for 16 h, and blood was collected from the fundus venous plexus. Before taking blood, the capillary was moistened with heparin, 0.5 ml of blood was collected from the fundus venous plexus, centrifuged at 3500 r/min for 10 min, and plasma was separated for testing. The supernatant was sucked, and the insulin was measured by using the ELISA method. The detailed operations were performed according to the specification of the kit.

The measurement of the insulin resistance: after the concentrations of fasting blood sugar and insulin have been measured, the insulin resistance was calculated by using the formula:

insulin resistance=fasting blood sugar*fasting insulin/22.5 (it is recently reported that when it is>2.6, it is determined that insulin resistance exists).

All of the data were statistical analyzed by using the SPSS16.0 software. All of the data obtained in the experiment were expressed by using mean value plus-minus standard deviation ($\bar{x} \pm s$). The mean values of the groups were compared in terms of the difference by using one-way ANOVA verification, wherein its $P<0.05$ indicates that the difference is significant. The result is as shown in Tables 2-6. At the 30th day and the 45th day after the modeling and intragastric administration, as compared with the normal control group, the body weights of the animals of the model group were significantly reduced, the fasting blood sugars were significantly increased, the sugar tolerances were reduced, the fasting serum insulins were not obviously influenced, and the insulin resistances were significantly increased.

Carrimycin can ameliorate the symptom of reducing of body weight of diabetes mouse, reduce the fasting blood sugar of mouse, and increase the sugar tolerance, does not obviously influence the fasting serum insulin, but can reduce the insulin resistance, which indicates that carrimycin has a good efficacy of reducing blood sugar.

TABLE 2 variation of body weights of the groups of the animal experiment (g) ($\bar{x} \pm s$)

| Group | Dosage (mg/kg) | Dosage | Body weight gain on 30th day | Body weight gain on 45th day |
|---|---|---|---|---|
| Normal control group | — | — | 6.63 ± 2.74 | 9.51 ± 2.72 |
| Model control group | — | — | 2.14 ± 1.97* | 0.58 ± 2.04* |
| Positive control group | 200 | 200 mg/kg | 5.94 ± 1.03# | 7.26 ± 1.48# |
| Administration group | 25 | 100 mg/kg | 3.52 ± 1.31# | 4.58 ± 1.18# |
| | 50 | 200 mg/kg | 4.75 ± 1.67# | 5.87 ± 1.36# |
| | 100 | 400 mg/kg | 5.81 ± 1.80# | 6.81 ± 1.37# |

*$p < 0.05$ as compared with the normal control group, #$p < 0.05$ as compared with the model control group, n = 8.

TABLE 3 variation of the blood sugars of the groups of the animal experiment (mmol/L) ($\bar{x} \pm s$)

| Group | Dosage (mg/kg) | 0 day | 30th day | 45th day |
|---|---|---|---|---|
| Normal control group | — | 5.28 ± 0.42 | 4.68 ± 0.97 | 4.81 ± 0.52 |
| Model control group | — | 17.84 ± 1.35*** | 22.62 ± 1.43*** | 20.16 ± 1.66* |
| Positive control group | 200 | 18.07 ± 1.26*** | 14.94 ± 1.03***# | 10.24 ± 1.07***## |
| Administration group | 25 | 17.95 ± 1.81*** | 16.52 ± 1.31***# | 14.58 ± 1.91*# |
| | 50 | 18.20 ± 1.54*** | 16.15 ± 1.67***# | 12.87 ± 1.81*# |
| | 100 | 17.98 ± 0.85*** | 15.81 ± 1.80***# | 11.81 ± 1.71***## |

*$p < 0.05$ as compared with the normal control group, $p < 0.01$ as compared with the normal control group, *$p < 0.001$ as compared with normal control group, #$p < 0.05$ as compared with the model control group, ##$p < 0.01$ as compared with the model control group, ###$p < 0.001$ as compared with the model control group, n = 8.

TABLE 4 influence by Carrimycin on the sugar tolerance of diabetes mouse ($\bar{x} \pm s$) (30th day)

| Group | Dosage (mg/kg) | Blood sugar value | | | |
|---|---|---|---|---|---|
| | | 0 h | 0.5 h | 2 h | AUC |
| Normal control group | — | 6.0 ± 0.7 | 7.9 ± 1.0 | 6.6 ± 1.0 | 14.3 ± 0.9 |
| Model control group | — | 14.0 ± 1.9** | 29.6 ± 2.8** | 20.6 ± 2.1*** | 49.1 ± 3.0*** |
| Positive control group | 200 | 14.6 ± 1.4** | 19.8 ± 1.8**## | 13.5 ± 1.9**# | 33.6 ± 2.7**# |
| Administration group | 25 | 14.4 ± 2.4** | 21.8 ± 2.2**# | 25.4 ± 3.0** | 44.6 ± 4.1** |
| | 50 | 14.7 ± 2.0* | 19.9 ± 2.8**## | 14.9 ± 2.0**# | 34.8 ± 3.2**# |
| | 100 | 13.5 ± 1.5* | 20.6 ± 2.1**## | 15.0 ± 2.1**# | 35.2 ± 2.4**# |

*$p < 0.05$ as compared with the normal control group, $p < 0.01$ as compared with the normal control group, *$p < 0.001$ as compared with the normal control group, #$p < 0.05$ as compared with the model control group, ##$p < 0.01$ as compared with the model control group, ###$p < 0.001$ as compared with the model control group, n = 8.

TABLE 5 influence by Carrimycin on the sugar tolerance of diabetes mouse ($\bar{x} \pm s$) (45th day)

| Group | Dosage (mg/kg) | Blood sugar value | | | |
|---|---|---|---|---|---|
| | | 0 h | 0.5 h | 2 h | AUC |
| Normal control group | — | 5.9 ± 0.7 | 6.9 ± 1.4 | 6.4 ± 1.3 | 13.2 ± 0.9 |
| Model control group | — | 14.4 ± 1.4** | 31.2 ± 2.1*** | 23.6 ± 1.8** | 52.5 ± 3.0*** |
| Positive control group | 200 | 14.1 ± 1.5** | 18.9 ± 1.7**# | 13.2 ± 1.7**# | 32.3 ± 2.1**# |
| Administration group | 25 | 14.7 ± 2.4** | 22.2 ± 3.1**# | 24.2 ± 2.6** | 44.0 ± 3.0**# |
| | 50 | 14.4 ± 2.0** | 20.2 ± 2.8**# | 15.1 ± 2.2**# | 35.1 ± 1.2**# |
| | 100 | 13.7 ± 1.5** | 19.4 ± 2.1**# | 14.9 ± 2.4**# | 34.0 ± 2.1**# |

*$p < 0.05$ as compared with the normal control group, $p < 0.01$ as compared with the normal control group, *$p < 0.001$ as compared with the normal control group, #$p < 0.05$ as compared with the model control group, ##$p < 0.01$ as compared with the model control group, ###$p < 0.001$ as compared with the model control group, n = 8.

TABLE 6 fasting insulin (mmol/L) and insulin resistance (IR) of the groups of the animal experiment

| Group | Dosage (mg/kg) | Fasting insulin (mmol/L) | Insulin resistance (IR) |
|---|---|---|---|
| Normal control group | — | 2.36 ± 0.07 | 0.50 |
| Model control group | — | 2.56 ± 1.28 | 2.29*** |
| Positive control group | 200 | 2.32 ± 1.26 | 1.06**### |
| Administration group | 25 | 2.38 ± 2.54 | 1.54**## |
| | 50 | 1.97 ± 1.65 | 1.13**## |
| | 100 | 1.93 ± 2.61 | 1.01**### |

*$p < 0.05$ as compared with the normal control group, $p < 0.01$ as compared with the normal control group, *$p < 0.001$ as compared with the normal control group, #$p < 0.05$ as compared with the model control group, ##$p < 0.01$ as compared with the model control group, ###$p < 0.001$ as compared with the model control group, n = 8.

TEST EXAMPLE 3

Influence by Carrimycin on the Model If injection of $A\beta_{1-42}$ into Bilateral CA1 Hippocampus of a SD Rat to Cause AD Experimental Animal:

Male healthy Sprague Dawley rats (grade SPF), with body weights of 220-260 g, commercially available from Liaoning Changsheng Biotechnology Co., Ltd., with the license number SOCK (liao) 2015-0001.

Experimental Drugs and Reagents:

Carrimycin $A\beta_{1-42}$: commercially available from Sigma, USA;

resveratrol: the Aladdin company (Lot#K1414052) (L.A., Calif., USA).

Experimental Instruments:

Stereotaxic apparatus: Stoelting, the United States, Model 51600 (Kiel, Wis., USA);

Morris water maze and automatic gathering and analyzing apparatus: Beijing Shuolinyuan Instruments Co. Ltd. (Beijing, China);

Y maze and automatic gathering and analyzing apparatus: Beijing Shuolinyuan Instruments Co. Ltd. (Beijing, China).

Operation Steps:

Grouping: male SD rats with body weights of 220-260 g were provided, adaptatively fed for 3 days, during which water drinking and food eating are free, circulating day and night for 12 h. The mice were randomly divided into 6 groups, a sham-operation control group, a model group, three groups were fed with 25, 50 and 100 mg/kg of carrimycin, and one group was fed with 30 mg/kg of the positive drug resveratrol.

Experimental process: $A\beta_{1-42}$ was dissolved by using a hexafluoroisopropanol/sterile normal-saline solution to obtain the concentration of 2 μg/μL, incubated and aged at 4° C. for 24 h to form a AO oligomer, and reserved. In the surgery, a rat was narcotized by using intraperitoneal injection of 3.5% of chloral hydrate (350 mg/kg), fixed on the stereotaxic apparatus. one shot was injected by using a microsyringe into the bilateral CA1 hippocampus with the bregma as the center, at the backward point at 3.6 mm and the leftward and rightward points at ±2.5 mm, with a needle insertion depth of 3.1 mm. 2.5 μL, (0.5 μL/min) was injected within 5 min into each side of the hippocampus, and the needle was retained for 5 min, to result in a rat dementia model. An equal volume of normal saline was injected by using the same operation method into the bilateral CA1 hippocampus of a rat of the sham-operation control group, which is the animal model selection: modeling by using lateral ventricle injection of $A\beta_{1-42}$; an equal volume of normal saline was injected by using the same operation method into the bilateral CA1 hippocampus of a rat of the sham-operation control group, wherein the amyloid plaque of β-amyloid protein (Aβ) is a currently generally acknowledged pathological marker of AD, and the employment of the above animal model for studying the effect of carrimycin on treating the disease of the central nervous system Alzheimer's disease has sufficient theoretical basis.

On the next day after the model was established, the sham-operation control group and the model group were administered intragastrically by using the corresponding solvents, the other experimental groups were administered intragastrically by using 25, 50 and 100 mg/kg of carrimycin and 30 mg/kg of the positive drug resveratrol. On the 12th day after $A\beta_{1-42}$ was injected into the hippocampus, the experiments of Y maze, new-object distinguishing and water maze were carried out in sequence. Continue to administer during the behavioral experiment 1 time per day till the behavioristics end.

The rat Y-maze experiment: on the 12th day after the administration, the Y-maze experiment was performed on the groups of rats. The rat Y-maze experiment aimed at investigating the influence by carrimycin on the spontaneous alternate movement and working memory of the rats. The apparatus is composed of three wood support arms with an included angle of 120 degrees therebetween, which are referred to as the arm A, the arm B and the arm C. In the experiment, the rats were placed into the tip of the arm A, and were permitted to freely enter and leave the three arms. The total time quantity of entering the arms and the order of entering the arms within 8 min of each of the rats were recorded. By using the continuous entering into the three different arms as one correct alternate reaction, the time quantity of the correct alternate reactions was recorded. The spontaneous alternate reaction rate is used to reflect the capacity of space working memory.

The rat new-object-distinguishing experiment: on the 14-15th day after the administration, the new-object-distinguishing experiment was performed on the groups of rats. The rat new-object-distinguishing experiment aims at investigating the influence by carrimycin on the figure distinguishing memory of the rats. The experimental apparatus is a black plastic circular open field with the diameter of approximately 60 cm and the height of 20 cm. This experiment was divided into an adapting phase and a test phase. In the adapting phase, 2~3 rats were placed into the open field each time, and were permitted to freely explore for 3 min to adapt for the environment, and the process was performed 2 times per day for 2 days. The test was performed on the third day, in which each time one rat was placed into the open field to firstly freely explore for 3min, and was then taken out, 2 same objects (A1, A2) were placed into the center of the open field, the rat was placed into the open field, and the durations (tA1, tA2) during which the rat exploreed the two objects within 5 min were recorded. After 1 h, the object A2 was replaced with a new object B, the rat was placed into the open field again, and the durations (tA1, tB) during which the rat explored the two objects were recorded. After 24 h, the object B was replaced with an object C, the rat was placed into the open field again, and the durations (tA1, tC) during which the rat explored the two objects were recorded. The standard of criterion of the exploring is that the rat points its nose towards the objects and has a distance to the objects no more than 1 cm, or touches the nose, licks the objects or touches the object by using a forepaw. The preferential index and the discrimination index to the new objects are calculated.

The formulas of calculating the preferential index are as follows:

preferential index (1 h)=$tB/(tA1+tB)$ preferential index (24 h)=$tC/(tA1+tC)$

The formulas of calculating the discrimination index are as follows:

discrimination index (1 h)=$(tB-tA1)/(tA1+tB)$ discrimination index (24 h)=$(tC-tA1)/(tA1+tC)$ The rat water-maze experiment: on the 16-20th day after the administration, the Morris water-maze experiment was performed on the groups of rats. The Morris water-maze experiment aims at investigating the influence by Carrimycin on the space studying memory disorder. The water-maze apparatus is composed of a black stainless-steel circular water pool with the diameter of 1.5 meters and the height of 50 centimeters and a circular metal platform with the diameter of 10 centimeters, and the platform can freely move. Before the experiment, the water pool was filled with water (water temperature 24±1° C.) to cause the water level to be above the platform by 1 centimeter. In the training phase, training is performed 1 time in the morning and afternoon per day for 6 days. The platform was placed in the fourth quadrant, a rat was placed into the water with the face facing the pool wall, and recording was performed for 90 seconds. If the rat finds the platform within 90 seconds, it is permitted to rest for 10 seconds on the platform, and if it cannot find the platform within 90 seconds, it is guided to the platform and rests for 10 seconds. After the training has ended, the test is performed, by removing the platform, and permitting the rat to freely swim for 90 seconds. A maze system automatically records the duration for which the rat stays in the original platform quadrant (the target quadrant).

Figure 2:
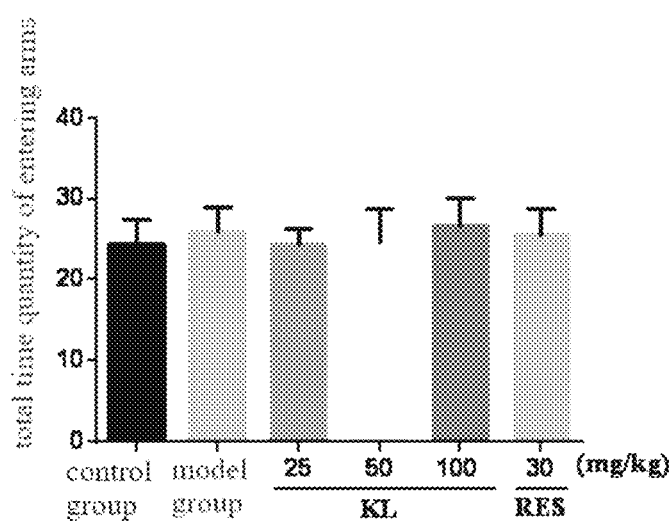
FIG. 2 is the total time quantities of entering the arms of the groups of rats in the rat Y-maze experiment according to the present disclosure.

Results:

The capacity of working memory of the rats from the Y-maze test: the experimental result indicates that, as compared with the sham-operation control group, the Y-maze spontaneous alternate reaction rate of the rats of the model group significantly decreased; and as compared with the model group, the Y-maze spontaneous alternate reaction rates of the rats of the carrimycin (25, 50 and 100 mg/kg) groups and the resveratrol (30 mg/kg) control group significantly increased (see FIG. 1). The total time quantities of entering the arms of the groups of rats did not have a significant difference (see FIG. 2). It can be obtained that carrimycin can ameliorate the damage on the working memory of the rats induced by $A\beta_{1-42}$.

Figure 3:
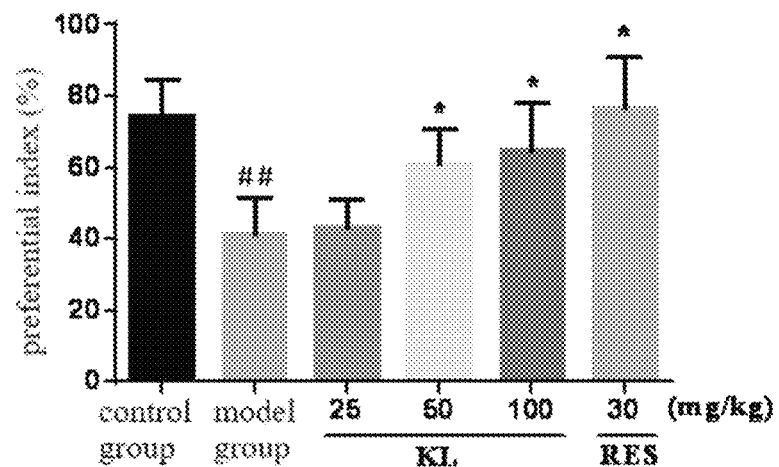
FIG. 3 is the preferential indexes on new objects after 1 h of the groups of rats in the rat new-object-distinguishing experiment according to the present disclosure.
Figure 4:
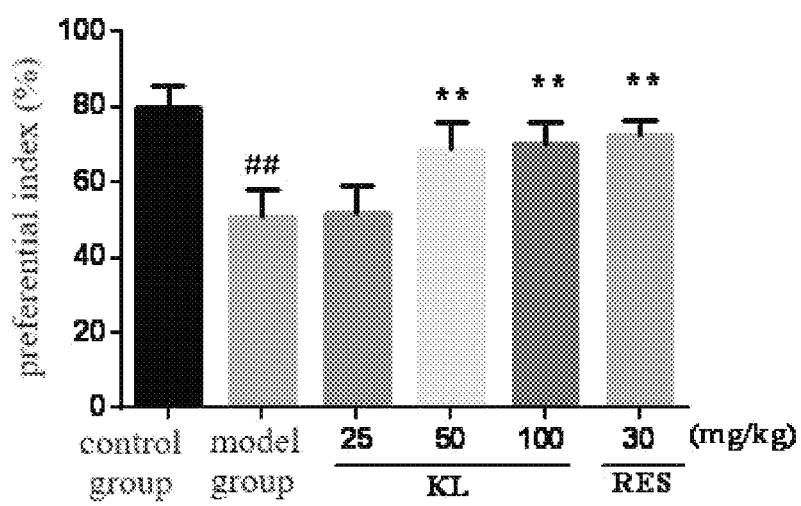
FIG. 4 is the preferential indexes on new objects after 24 h of the groups of rats in the rat new-object-distinguishing experiment according to the present disclosure.
Figure 5:
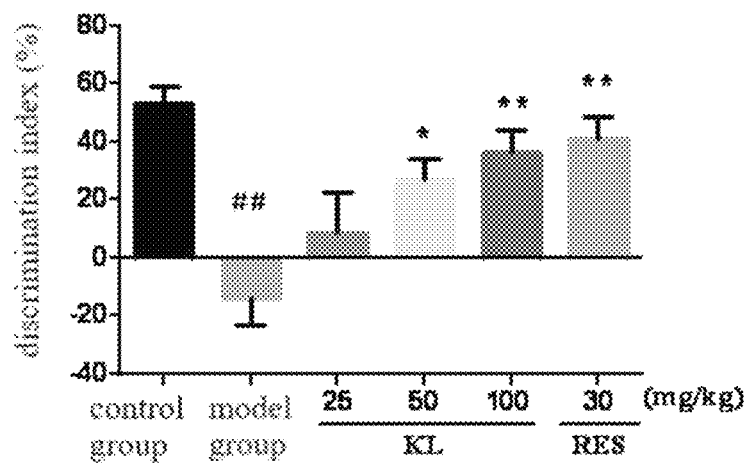
FIG. 5 is the discrimination indexes on new objects after 1 h of the groups of rats in the rat new-object-distinguishing experiment according to the present disclosure.
Figure 6:
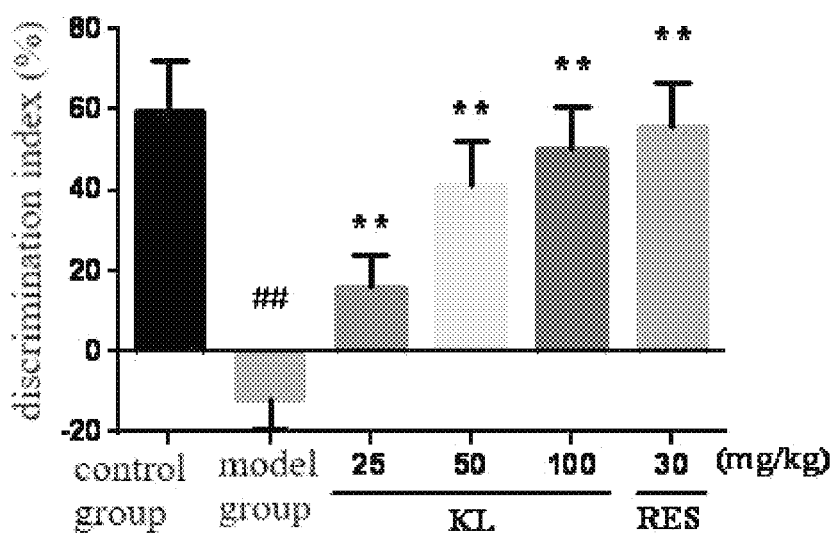
FIG. 6 is the discrimination indexes on new objects after 24 h of the groups of rats in the rat new-object-distinguishing experiment according to the present disclosure.

The capacity of figure memory of the rats from the new-object-distinguishing experiment test: the experimental result indicates that the discrimination indexes on the two same objects A1 and A2 of the groups of rats do not have an obvious difference (see Table 7). In the new-object-distinguishing experiment, as compared with the sham-operation control group, the preferential index and the discrimination index on the new objects of the rats of the model group, after 1 h and 24 h, significantly decreased; and as compared with the model group, all of the preferential indexes (see FIGS. 3 and 4) and the discrimination indexes (see FIGS. 5 and 6) on the new objects of the rats of the carrimycin and resveratrol groups, at 1 h and 24 h, significantly increased. Therefore, carrimycin can ameliorate the damage on the figure memory of the rats induced by $A\beta_{1-42}$.

TABLE 7 the test result of the discrimination index on A1 and A2 in the new-object-distinguishing experiment test of the rats induced by $A\beta_{1-42}$ (N = 4-5, mean value ± standard error)

| Group | Dosage (mg/kg) | Discrimination index on A1 and A2 (%) |
|---|---|---|
| Control | — | 45.34 ± 9.24 |
| Model | — | 49.24 ± 8.96 |
| Carrimycin | 25 | 43.65 ± 7.59 |
|  | 50 | 48.98 ± 6.35 |
|  | 100 | 54.76 ± 4.88 |
| Resveratrol | 30 | 52.87 ± 5.43 |

Figure 7:
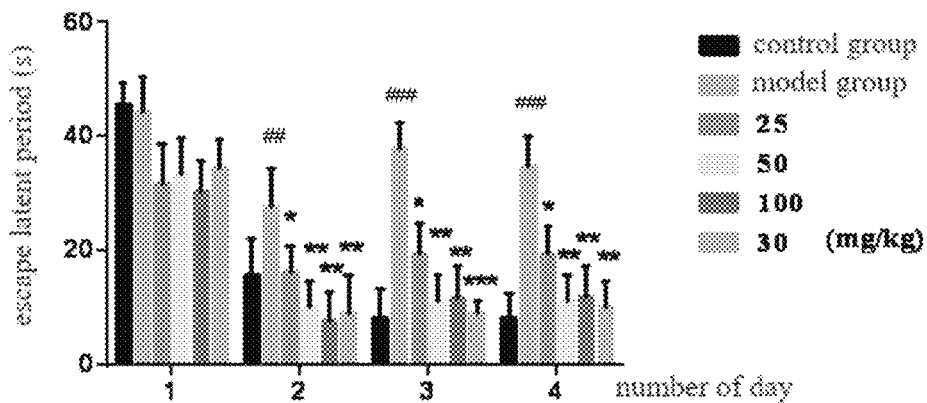
FIG. 7 is the escape latent periods of the groups of rats in the rat water-maze experiment according to the present disclosure.

The capacity of studying memory of the rats from the Morris water-maze test: the experimental result indicated that, in the experiment of locating and navigation, as the time quantity of the training increased, the escape latent periods of all of the groups of the experimental rats were shortened, which indicated that the capacity of space exploration and studying of all of the rats were improved. On the 2nd day of the experiment, as compared with the sham-operation control group, the escape latent periods of the rats of the model group were significantly prolonged; and as compared with the model group, the escape latent periods of the carrimycin groups and the resveratrol group significantly decreased. On the 3rd and 4th days, such a trend was maintained (see FIG. 7).

Figure 8:
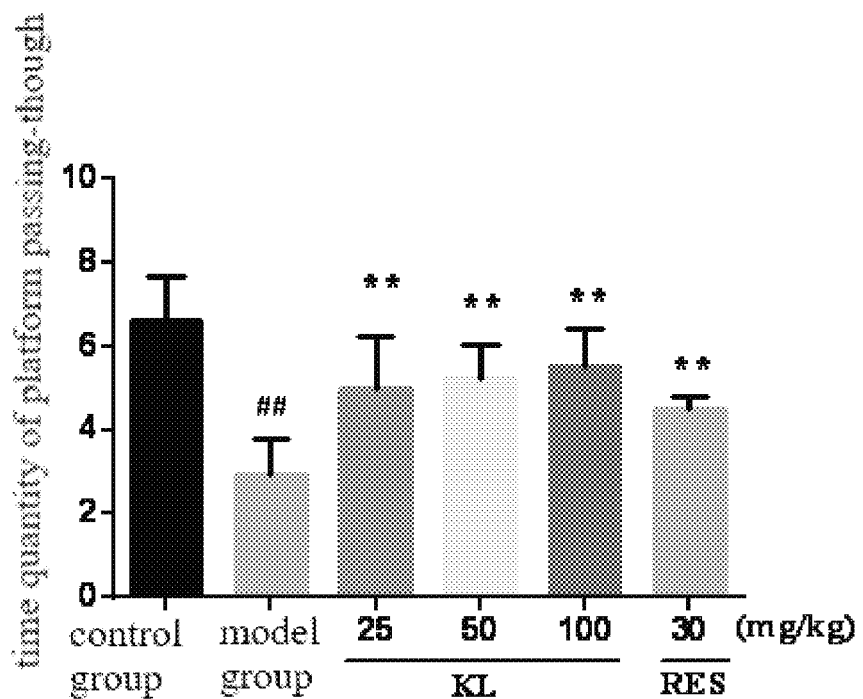
FIG. 8 is the time quantities of the platform passing-though of the groups of rats in the rat water-maze experiment according to the present disclosure.
Figure 9:
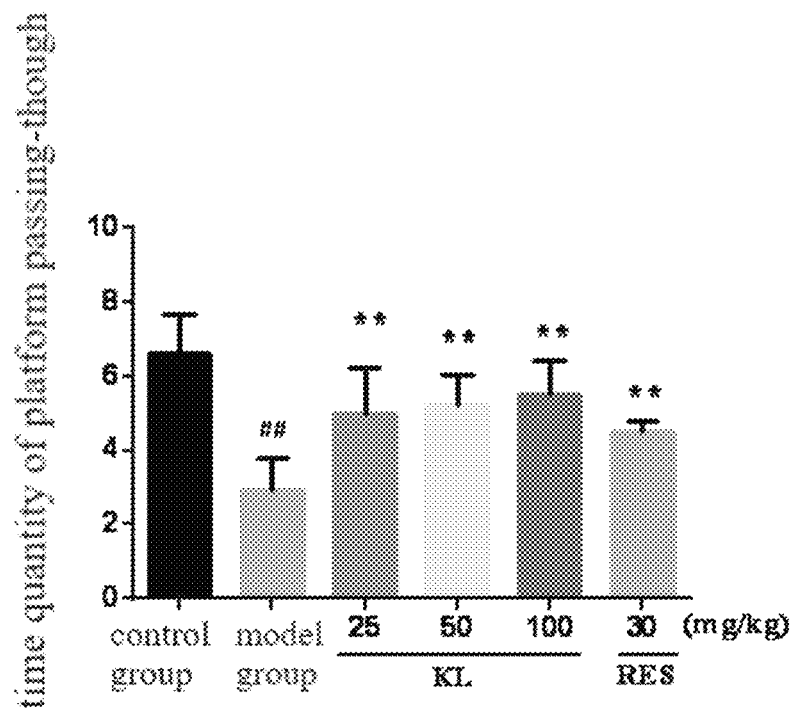
FIG. 9 is the swimming speeds of the groups of rats in the rat water-maze experiment according to the present disclosure.

The result of the space exploration experiment shows that, as compared with the sham-operation control group, the time quantity of passing through of the platform of the rats of the model group significantly decreased; as compared with the model group, the time quantities of passing through of the platform of the carrimycin groups and the resveratrol group significantly increased (see FIG. 8); and the swimming speeds of the groups of rats did not have a significant difference (see FIG. 9), which indicated that carrimycin and resveratrol could increase the time quantity of passing through of the platform of the rats. The experimental result indicated that carrimycin could ameliorate the damage on the capacity of studying memory and space exploration of the rats induced by $A\beta_{1-42}$.

The above experiments prove that the drug of the present disclosure has a good effect of treating the disease of the central nervous system Alzheimer's disease, which provides the theoretical basis for the application and clinical promotion of the drug of the present disclosure in the treatment of diseases of the central nervous system, and has important economic benefits and social benefits.

TEST EXAMPLE 4

Determining, by using Life Experiment, whether Carrimycin has the Effect of Prolonging the Life Span of *Caenorhabditis elegans*

Experiment materials, reagents and instruments
1.1 Strain and Nematode
*E. coli* OP50, preserved by laboratory of Shenyang Pharmaceutical University *C. elegans* N2, preserved by laboratory of Shenyang Pharmaceutical University
1.2 Main Reagents

| | |
|---|---|
| anhydrous ethanol (analytically pure) | Beijing Chemical Factory |
| sodium hydroxide (analytically pure) | Beijing Chemical Factory |
| tryptone | OXOID |
| agar powder | Dingguo Biological Engineering Company |
| yeast powder | OXOID |
| sodium chloride (analytically pure) | Beijing Chemical Factory |
| calcium chloride (analytically pure) | Beijing Chemical Factory |
| cholesterol (analytically pure) | Shanghai Chemical Reagent Company |
| magnesium sulfate (analytically pure) | Beijing Chemical Factory |
| potassium sulphate (analytically pure) | Beijing Chemical Factory |
| potassium dihydrogen phosphate (analytically pure) | Shanghai Reagent No. 2 Factory |
| disodium hydrogen phosphate (analytically pure) | Beijing Chemical Factory |
| Dimethyl sulfoxide | |

1.3 Main Instruments

| | |
|---|---|
| gel imager | ImageMaster Pharmacia company |
| clean bench | Suzhou Cleaning Equipment Limited Company |
| biochemical incubator | Harbin Donglian Electronic Technology Co. LTD |
| 752-model spectrophotometer | Shanghai Precise Scientific Instruments Limited Company |
| optical microscope | OLYMPUS |
| constant-temperature air-bath vibrator | Harbin Donglian Electronic Technology Co. LTD |
| refrigerated centrifuge | Hettich zentrifug |
| electrically heated thermostatic | Hebei Huanghua Aerospace |

-continued

| | |
|---|---|
| water bath | Instrumentation Factory |
| high-temperature sterilizing oven | Sanyo, Japan |
| electrothermal blowing dry box | Nanjing Laboratory Instrument Factory |
| electronic analytical balance | SHIMADZU |

The operation steps are as follows:
1.1 The Culturing of the Nematode

The hermaphroditic nematode was fed on a standard nematode growth medium (NGM) coated with Escherichia coli OP50, the culturing temperature was 20° C. The growth condition of the nematode was observed, and the nematode were periodically transferred to a new NGM medium coated with *E. coli* OP50.

1.2 The Synchronization of the Nematode

Firstly, several nematodes in the spawning period were put in the same panel (the particular quantity was determined according to the required quantity of the nematodes, and generally one nematode in the spawning period could lay approximately 8 eggs within one hour). After 30 min, the nematodes in the panel were picked out, and the eggs in the panel were incubated, and thus can be in the same growth period.

1.3 The Life-Cycle Experiment

In order to systematically and accurately measure the lives of the nematodes, an administration group and a control group were preset by using the method of liquid culture. The drug concentration of the administration group was selected, and the drug was diluted by using normal saline to the required concentration. A 24-well plate was employed, and 420 microliters of liquid culture liquid, 30 microliters of bacteria solution and 50 microliters of the carrimycin were added into each of the wells (the control group used an S-medium liquid medium), to cause the total volume of the liquid in each of the wells to be 500 microliters. 25 synchronized nematodes were added into each of the wells, and after every other 24 h, the survival nematodes were transferred to the next one new well with the same condition of the nutrient solution, till all of the nematodes died. The nematodes that had no reaction to mechanical stimulus and did not swallow food or excrete were determined as dead, every other 24 h after the transferring, the quantities of the nematodes that were surviving of each of the groups were recorded, and the longest surviving day quantity and the average surviving day quantity of the nematodes of each of the groups were counted.

Figure 10:
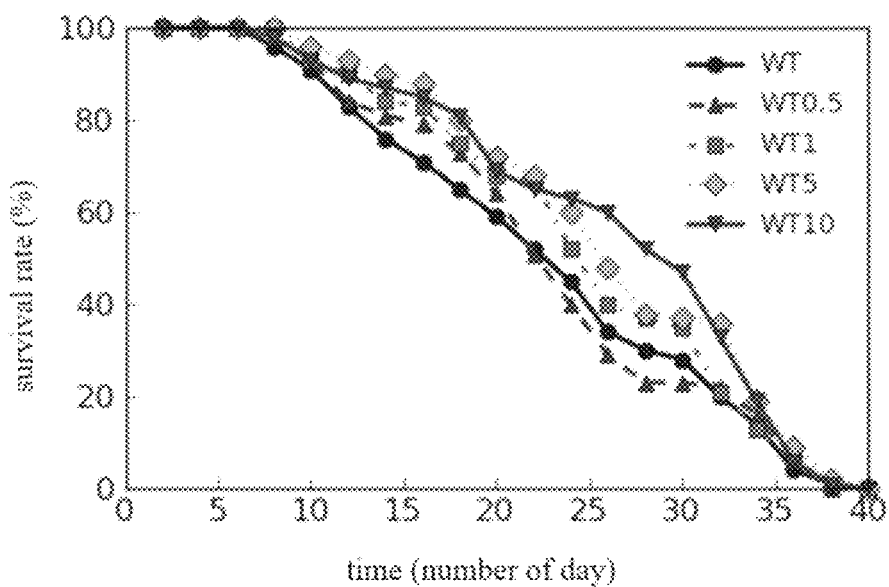
FIG. 10 is the influence on the life cycle after the administration of carrimycin.

The experiment result can be seen in Table 8 and FIG. 10, which indicate that carrimycin can prolong the average life span of *Caenorhabditis elegans,* and has an obvious effect at the concentration of 5 μg/ml.

TABLE 8

| Concentration (μg/ml) | Mean life span ± SD (days) | N |
|---|---|---|
| 0 | 23.38 ± 0.90 | 25 |
| 0.5 | 23.64 ± 0.84 | 25 |
| 1 | 25.32 ± 0.83 | 25 |
| 5 | 26.72 ± 0.82* | 25 |
| 10 | 26.97 ± 0.87* | 25 |

TEST EXAMPLE 5

Determining, by Testing the Movement-Capacity Indicator, whether Carrimycin has the Effect of Prolonging the Life Span of *Caenorhabditis elegans*

Reagents: the same as those of Test Example 4
Instruments: the same as those of Test Example 4
Experimental subject: *Caenorhabditis elegans*
Process: the nematodes of the administration group and the nematodes of the control group were synchronization-treated, and a certain quantity of synchronized nematodes of each groupwere obtained for being cultured. When they had entered the adult stage (generally the third day), they were administered with carrimycin, and after 48 hours, their movement speeds were measured. Every 24 hours, 10 nematodes were randomly selected from each of the groups, the distances by which they moved within a time period were measured, and the quantities of the peaks that the nematodes walked through within 20 s were recorded.
Experimental result: the administration of 5 µg/ml and 10 µg/ml of carrimycin can significantly increase the action and movement capacity of the nematodes, which can be seen in FIGS. 11-*a* and 11-*b*.

TEST EXAMPLE 6

Determining, by Testing the Survival Rate of *Caenorhabditis elegans* in a Hot-Shock Condition, whether Carrimycin has the Effect of Prolonging the Life Span of *Caenorhabditis elegans*

Figure 12:
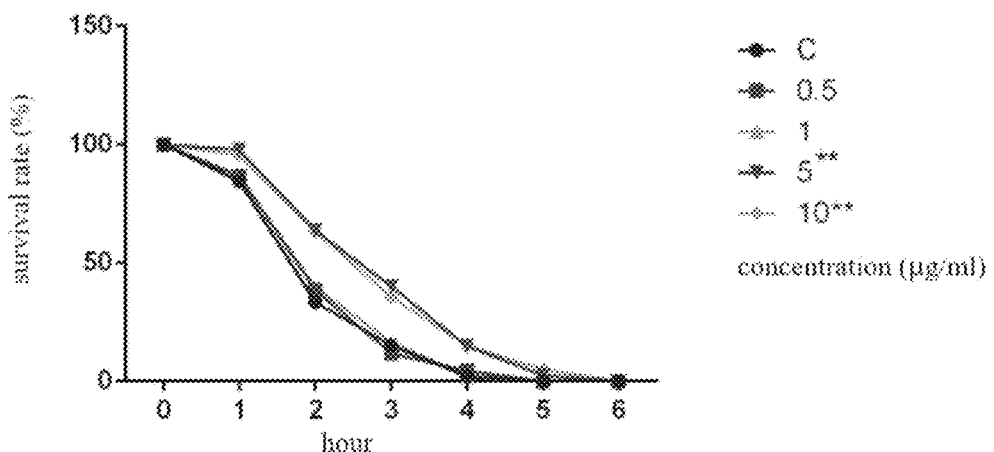
FIG. 12 is the assay of the survival rate under heat-stress reaction after the administration of carrimycin.

Reagents: the same as those of Test Example 4
Instruments: the same as those of Test Example 4
Experimental subject: *Caenorhabditis elegans*
Process: the nematodes were synchronously cultured in a normal culturing condition to phase L4, a certain quantity of hermaphroditic nematodes were added into a 30 mm disposable culture dish with 2 ml S-medium, and the culturing was continued at 20° C. The nutrient solution contains carrimycin, *E. coli* OP50 thallus (OD600=0.2-0.3) and 50 µM FUdR (for preventing the growth of the offspring nematodes). The control group was cultured by using an S-medium liquid medium that did not contain carrimycin. It should be noted that the nematodes should be transferred to a culture dish containing a fresh medium every day to renew the nutrient solution. After 48 h, the nematodes were transferred to 37° C., the culturing was continued for 10 h, and the quantity of the nematodes surviving after the culturing ends was recorded as the survival rate of the experiment. The experiment should be in parallel repeated 2-3 times, and the average value is used as the final result of the survival rate.
Experimental result: it can be seen from the figure that, as compared with the control group, carrimycin can significantly enhance the capacity of heat resistance of the nematodes, and prolong the mean survival time at 37° C. of the nematodes, which can be seen in FIG. 12.

TEST EXAMPLE 7

Determining, by Testing the Survival Rate of *Caenorhabditis elegans* in an Ultraviolet Irradiation Experiment, whether Carrimycin has the Effect of Prolonging the Life Span of *Caenorhabditis elegans*

Figure 13:
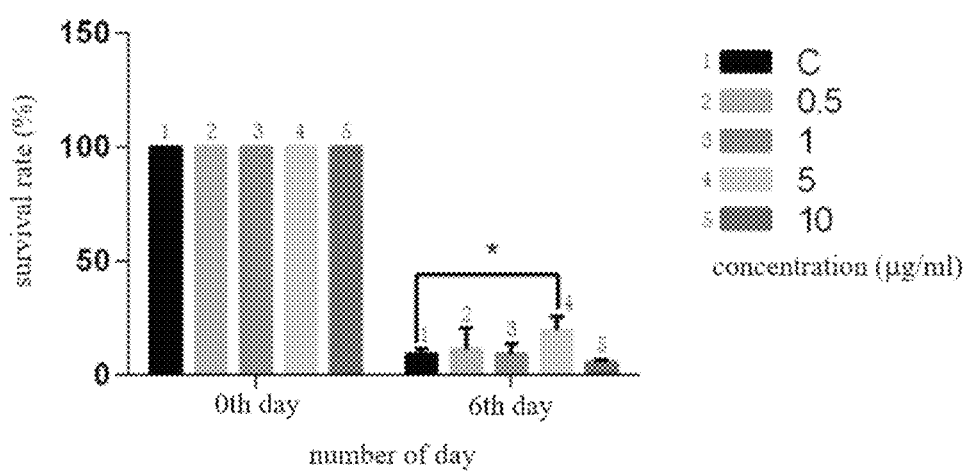
FIG. 13 is the assay of the survival rate under UV irradiation after the administration of carrimycin.

Reagents: the same as those of Test Example 4
Instruments: the same as those of Test Example 4
Experimental subject: *Caenorhabditis elegans*
Process: the experimental culture plates of the nematodes from the synchronization to the phase I4 were fixed under an ultraviolet lamp, pre-experiment irradiation was performed for 240 s, and the quantities of the dead and surviving nematodes were recorded. The criterion of the death of the nematodes is the same as that of the life experiment. The ultraviolet wavelength was 254 nm, the height of the ultraviolet lamp above the culture plates was 15 cm, and the power was $1 \times 10^{-3}$ W/cm$^3$. The experimental groups were a control group and an administration group.
Experimental result: it can be known from the figure that carrimycin has a certain effect for resisting the damage caused by ultraviolet irradiation and oxidation, which can be seen in FIG. 13.
Result
The experiment was repeated at least 3 times. The results were given in the form of mean values and standard deviations. The significance test was mainly t-test. All of the statistical analysis and charting of the data employ Excel and the software SPSS16.0.

TEST EXAMPLE 8

Testing whether Carrimycin can Reduce the In-Vivo Accumulation of Lipofuscin in Wild-Type *Caenorhabditis elegans*

Process: culturing was performed according to the culturing method of the life experiment for 10 days, 15 days and 20 days. The nematodes were narcotized by using NaN$_3$, and were inversely placed under a fluorescence microscope with the excitation light of 340-380 nm and the emitted light of 430 nm. The in-vivo levels of lipofuscin of the nematodes were observed, fluorescence pictures were photographed, and the in-vivo lipofuscin fluorescence levels of the nematodes wereanalyzed and processed by using the software ImageJ.
Because of the accumulation and aggregation of cross-linking proteins and so on, lipofuscin is deposited in the cells of various tissues and organs of the human body, which results in the slowing down of cellular metabolism and the decrease of activity, thus causing the decline of the functions of the organs of the human body to result in senility. Therefore, lipofuscin is regarded as a sign of senility. Lipofuscin has the characteristic of autofluorescence, and by observing the nematodes under the fluorescence microscope, their degrees of senility can be determined according to their fluorescence intensities. The measurement result can be seen in FIGS. 14-*a* and 14-*b*. The result indicated that the accumulated amount of lipofuscin of the administration group significantly decreased as compared with the control group.

TEST EXAMPLE 9

Study on the Mechanism of the Influence by Carrimycin on the Life Span of the Nematodes The sod-3 content assay indicated that after the administration the in-vivo expression quantity of sod-3 of the nematodes of the administration group decreased, and the lipofuscin fluorescence content indicated that after the administration the lipofuscin content of the administration group decreased. The present disclosure investigates whether Carrimycin influences the upstream genes daf-16 and daf-15 of sod-3.

1. Carrimycin can Increase the Expression of the Anti-Senility Gene Sod-3 of the Nematodes In Vivo Process: in this experiment the expression quantity of sod-3 was observed by using a nematode strain CF1553 with a gfp label. Nematodes that had entered the maturity were continuously treated by using Carrimycin for 6 days, two groups of nematodes were narcotized by using 10 mM of sodium azide, and fixed in 5% agar gel, and then the fluorescence intensities of the nematodes were observed and photographed by using a fluorescence microscope with the excitation wavelength of 488 nm and the emission wavelength of 500 nm-530 nm. The fluorescence intensities were quantitatively analyzed by using the software ImageJ. The sample size of the nematodes of each of the groups was 15. The experiment was repeated twice.

According to the theory of free radical and senility, ROS is the main reason for organism aging and diseases. Along with the process of senility, the free radicals in the nematodes in vivo gradually increase. The present disclosure has found out by the investigation that carrimycin can enhance the capacity of heat resistance of the wild-type nematodes, and enhance the intracellular stress resistance of the nematodes. Therefore, the present inventor postulates whether carrimycin resists senility by influencing the antioxidant gene sod-3. After continuously treating CF1553 (sod-3:: GFP) type nematodes by using carrimycin for 6 days, by observing by using a fluorescence microscope, it is found out that the expression quantity of the green fluorescence proteins of the nematodes of the administration group significantly increases compared with the nematodes of the control group. The result can be seen in FIG. 15. The result indicated that carrimycin might prolong the life span by increasing the antioxidant gene sod-3 to reduce the level of ROS of the nematodes in vivo.

2. Carrimycin can Influence the Distribution of DAF-16 in Cells

Process: 30 of each of the groups of TJ356 (DAF-16:: GFP) nematodes in the phase L4 were placed on an NGM panel where OP50 was growing vigorously, and laid eggs for 3-4 hours, then the synchronization of the nematodes ends. After the eggs had grown into imagos, the 30 of each of the groups were administered in groups. The state of nucleus entering of TJ356 nematode DAF-16 on the 6th day after the administration was measured, and the state of nucleus entering of DAF-16 was observed by using an inversely placed fluorescence microscope.

Whether DAF-16 aggregates in the cell nucleus or disperses in the cytoplasm is directly related to its activity. Normally DAF-16 is located in the cytoplasm in vivo, and if it is in an environment of external stress, different proteins are activated, which in turn promotes to enter the cell nucleus to perform the transcription function to start the downstream gene expression to prolong the life span of the nematodes. Studies show that both of the lack of insulin and oxidative stress can cause DAF-16 to aggregate in the cell nucleus, to improve the capacity of the nematode to resist oxidative stress and prolong the life span of the nematode.

Because the prolonging of the nematode life span by carrimycin is related to DAF-16, the present inventor postulates that carrimycin might influence the distribution of DAF-16 in the cell. The present disclosure investigates the distribution of DAF-16 in the cell by using DAF-16::GFP genetically modified nematode TJ356. Nematodes that have immediately entered the adult stage were treated by using Carrimycin, and on the 6th day after the administration, they were observed by using an inversely placed fluorescence microscope.

As a result, it was found out that the green fluorescence of the TJ356 nematodes treated by carrimycin was concentrated in the cell nucleus in the state of dot shaped aggregation, while the green fluorescence of the TJ356 nematodes that were not treated by carrimycin were dispersed throughout the entire cell. On the 6th day after the treatment by using 5 and 10 μg/ml of carrimycin, the aggregation of DAF-16 in the cell nucleus significantly increased as compared with the untreated nematodes. That indicated that carrimycin could facilitate DAF-16 to enter the cell nucleus, which can be seen in FIGS. 16-a and 16-b.

The invention claimed is:

1. A method for treating Alzheimer's disease or treating diabetes, comprising administering to a subject an effective amount of a medicament comprising one of carrimycin, isovalerylspiramycin I, isovalerylspiramycin II and isovalerylspiramycin III, or a combination of two or three of isovalerylspiramycin I, isovalerylspiramycin II and isovalerylspiramycin III.

2. The method according to claim 1, wherein the method for treating Alzheimer's disease includes reducing hydrolysis of acetylcholine, ameliorating cognitive disorder and dyskinesia, protecting intracerebral nerve cell, not reducing body weight, improving immunity or improving leukocyte; and the method for treating diabetes includes treating diabetes type I or diabetes type II or specific types of diabetes.

3. The method according to claim 2, wherein the method for treating diabetes includes facilitating insulin secretion or reducing blood sugar or protecting islet β cell or treating diabetes and maintaining body weight.

4. The method according to claim 1, wherein the medicament further comprises a second active ingredient;

when treating Alzheimer's disease, the second active ingredient is at least one of anti-Alzheimer-disease drugs; and when treating diabetes, the second active ingredient is at least one of antidiabetic drugs.

5. The method according to claim 1, wherein the medicament and a pharmaceutically acceptable carrier are made into a clinically acceptable formulation.

6. The method according to claim 5, wherein a dosage of the medicament is in a range from 10 to 1500 mg/kg.

7. The method according to claim 6, wherein, the dosage of the medicament is in a range from 50 to 1000 mg/kg.

8. The method according to claim 6, wherein, the dosage of the medicament is in a range from 100 to 500 mg/kg.

9. The method according to claim 5, wherein, the clinically acceptable preparation is selected from a tablet, a capsule, a pill, an injection, a sustained-release preparation or a particulate administration system.

10. A method for treating Alzheimer's disease, or treating diabetes, comprising administering to a subject an effective amount of a combined product comprising a first medicament, wherein an active ingredient of the first medicament comprises one of carrimycin, isovalerylspiramycin I, isovalerylspiramycin II and isovalerylspiramycin III, or a combination of two or three of isovalerylspiramycin I, isovalerylspiramycin II and isovalerylspiramycin III.

11. The method according to claim 10, wherein the combined product further comprises a second medicament;

when treating Alzheimer's disease, the second medicament is at least one of drugs for treating Alzheimer's disease; and when treating diabetes, the second medicament is at least one of drugs for treating diabetes.

12. The method according to claim 11, wherein a mass ratio of the first medicament to the second medicament is 1~99:99~1.

13. The method according to claim 12, wherein the mass ratio of the first medicament to the second medicament is 5~95:95~5.

14. The method according to claim 12, wherein the mass ratio of the first medicament to the second medicament is 10~90:90~10.

15. The method according to claim 12, wherein the mass ratio of the first medicament to the second medicament is 20~80:80~20.

16. The method according to claim 11, wherein the drugs for treating Alzheimer's disease include a drug acting on a cholinergic system; and the drugs for treating diabetes include a biguanide hypoglycemic drug.

* * * * *